(12) United States Patent
Ancona et al.

(10) Patent No.: US 10,466,190 B1
(45) Date of Patent: Nov. 5, 2019

(54) THERMALLY PULSED CHEMIELECTRIC POINT SENSING

(71) Applicant: The Government of the United States of America, as represented by the Secretary of the Navy, Arlington, VA (US)

(72) Inventors: Mario Ancona, Alexandria, VA (US); F. Keith Perkins, Alexandria, VA (US); Arthur W. Snow, Alexandria, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/139,439

(22) Filed: Sep. 24, 2018

(51) Int. Cl.
*G01N 25/48* (2006.01)
*B01D 53/04* (2006.01)
(Continued)

(52) U.S. Cl.
CPC ..... *G01N 25/4826* (2013.01); *B01D 53/0462* (2013.01); *G01N 1/405* (2013.01);
(Continued)

(58) Field of Classification Search
CPC .... G01N 25/4826; G01N 1/405; G01N 30/32; G01N 2030/008; G01N 2030/326; B01D 53/0462
See application file for complete search history.

(56) References Cited

U.S. PATENT DOCUMENTS

| 6,171,378 B1 * | 1/2001 | Manginell | G01N 30/12 55/DIG. 5 |
| 6,238,085 B1 * | 5/2001 | Higashi | G01N 25/18 374/10 |

(Continued)

OTHER PUBLICATIONS

Arthur W. Snow, F. Keith Perkins, Mario G. Ancona, Jeremy T. Robinson, Eric S. Snow, and Edward E. Foos, "Disordered Nanomaterials for Chemielectric Vapor Sensing: A Review," IEEE Sensors Journal, vol. 15, No. 3, Mar. 2015, pp. 1301-1320.

(Continued)

*Primary Examiner* — Lisa M Caputo
*Assistant Examiner* — Philip L Cotey
(74) *Attorney, Agent, or Firm* — US Naval Research Laboratory; Joslyn Barritt

(57) ABSTRACT

An apparatus and method for producing chemielectric point-sensor systems with increased sensitivity and increased selectivity. The chemielectric sensor system includes a sensor/heater assembly, where the sensor is a chemielectric sensor whose resistance or capacitance changes upon exposure to chemical analytes. The heater functionality applies a programmed sequence of one or more thermal pulses to the sensor to quickly raise its temperature. After each thermal pulse ends the change in resistivity of the sensor is measured. Such data as a function of the pulse time and temperature are recorded and analyzed to determine the chemical composition (selectivity) and concentrations in the ambient vapor by comparison to a library dataset. The sensor operation with fast thermal pulses also allows operation at higher frequencies where the noise is lower and hence sensitivity is improved.

17 Claims, 15 Drawing Sheets

(51) Int. Cl.
*G01N 30/32* (2006.01)
*G01N 1/40* (2006.01)
*G01N 30/00* (2006.01)

(52) U.S. Cl.
CPC ....... *G01N 30/32* (2013.01); *G01N 2030/008* (2013.01); *G01N 2030/326* (2013.01)

(56) References Cited

U.S. PATENT DOCUMENTS

| | | | |
|---|---|---|---|
| 8,409,510 B2* | 4/2013 | McGill | B01L 3/502753 422/527 |
| 8,736,000 B1* | 5/2014 | Manginell | G01N 27/221 257/215 |
| 2005/0095722 A1* | 5/2005 | McGill | B01L 3/502753 436/174 |
| 2009/0028208 A1* | 1/2009 | Martin | G01N 1/405 374/1 |
| 2009/0272896 A1* | 11/2009 | Belyakov | G01N 27/64 250/286 |
| 2010/0055801 A1* | 3/2010 | Yi | G01N 27/18 436/149 |
| 2010/0101301 A1* | 4/2010 | McBrady | G01N 33/0011 73/23.21 |
| 2010/0236341 A1* | 9/2010 | Martin | G01N 1/405 73/863.12 |
| 2011/0010107 A1* | 1/2011 | Fedder | G01N 27/127 702/22 |
| 2013/0114082 A1* | 5/2013 | Sailor | G01N 21/171 356/402 |
| 2015/0253265 A1* | 9/2015 | Whitten | G01N 25/20 506/9 |
| 2015/0268207 A1* | 9/2015 | Motayed | G01N 33/0031 506/13 |
| 2017/0153193 A1* | 6/2017 | Whitten | G01N 25/20 |
| 2017/0153199 A1* | 6/2017 | Patel | G01N 27/125 |
| 2018/0313800 A1* | 11/2018 | Rogers | G01N 33/0016 |

OTHER PUBLICATIONS

P. A. Redhead, "Thermal desorption of gases," Vacuum 12, 203 (1962).

J. Goering, E. Kadossov, and U. Burghaus, "Adsorption kinetics of alcohols on single-wall carbon nanotubes: An ultrahigh vacuum surface chemistry study," J. Phys. Chem. C 112, 10114 (2008).

R. L. Grimm, N. M. Ballentine, C. Knox, and J. C. Hemminger, "D2O water interaction with mixed alkane thiol monolayers of tuned hydrophobic and hydrophilic character," J. Phys. Chem. C 112, 890 (2008).

L.H. Dubois, B.R. Zegarski, and R.G. Nuzzo, "Fundamental studies of microscopic wetting on organic surfaces. 2. Interaction of secondary adsorbates with chemically textured organic monolayers," J. Am. Chem. Soc. 112 570 (1990) (organic monolayers).

J. S. Suehle, R. E. Cavicchi, M. Gaitan, and S. Semancik, "Tin oxide gas sensor fabricated using CMOS micro-hotplates and in-situ processing," IEEE Elect Dev. Lett. 14, 118 (1993).

B. Raman, R. Shenoy, D. C. Meier, K D. Benkstein, C. Mungle, and S. Semancik, "Detecting and recognizing chemical targets in untrained backgrounds with temperature programmed sensors," IEEE Sensors J. 12, 3238 (2012).

A. Vergara, K. D. Benkstein, C. B. Montgomery, and S. Semancik, "Demonstration of fast and accurate discrimination and quantification of chemically similar species utilizing a single cross-selective chemiresistor," Anal. Chem. 86, 6753 (2014).

L. R. Senesac, D. Yi, A. Greve, J. H. Hales, Z. J. Davis, D. M. Nicholson, A. Boisen, and T. Thundat, "Micro-differential thermal analysis detection of adsorbed explosive molecules using microfabricated bridges," Rev. Sci. Instr. 80, 035102 (2009).

J. W. Grate and B. M. Wise, "A Method for Chemometric Classification of Unknown Vapors from the Responses of an Array of Volume-Transducing Sensors," Anal. Chem. 2001, 73, 2239-2244.

S. Zampolli, I. Elmi, F. Mancarella, P. Betti, E. Dalcanale, G. C. Cardinali, and M. Severi, "Real-time monitoring of sub-ppb concentrations of aromatic volatiles with a MEMS-enabled miniaturized gas-chromatograph," Sensors and Actuators B 141 (2009) 322-328.

I. Voiculescu, M. Zaghloul, and N. Narasimhan, "Microfabricated chemical preconcentrators for gas-phase microanalytical detection systems," Trends in Analytical Chemistry, vol. 27, No. 4, 2008, pp. 327-343.

W. Kruppa, M. G. Ancona, R. W. Rendell, A. W. Snow, E. E. Foos, and R. Bass, "Electrical noise in gold nanocluster sensors," Applied Physics Letters 88, 053120 (2006).

N. M. Vörös, R. Patakfalvi, and I. Dëkány, "Alkylthiol-functionalized gold nanoparticles for sensing organic vapours: The connection between the adsorption isotherm and the sensor resistance," Coll. and Surf. A: Physicochem. and Eng. Aspects 329 (2008), 205-211.

K. Y. Foo and B. H. Hameed, "Insights into the modeling of adsorption isotherm systems," Chemical Eng. Journ. 156, 2 (2010).

M. G. Ancona, A. W. Snow, F. K. Perkins, B. Pate, and D. Park, "Analyte kinetics in a nanocluster-based chemiresistor: A case study," Sensors & Actuators B 177, 936-946 (2013).

H. Woltjen and A. W. Snow, "Colloidal metal-insulator-metal ensemble chemiresistor sensor," Anal. Chem. 70 (1998) 947-949.

A. A. Balandin, "Low-frequency 1/f noise in graphene devices," Nature Nanotechnology 8 (2013), 549-555.

J. T. Robinson, F. K. Perkins, E. S. Snow, Z. Q. Wei, and P. E. Sheehan, "Reduced Graphene Oxide Molecular Sensors," Nano Letters 8, 3137-3140 (2008).

\* cited by examiner

| Analyte vapor | Structure | Desorption threshold |
|---|---|---|
| NO$_2$ | O=N=O | 55mW |
| nitromethane | H$_3$C—NO$_2$ | 36 |
| 2-nitrotoluene | CH$_3$-C$_6$H$_4$-NO$_2$ | 30 |

THERMALLY PULSED CHEMIELECTRIC POINT SENSING

TECHNICAL FIELD

The present disclosure concerns the design and improvement of chemielectric vapor point sensor systems for detecting vapor analytes by exploiting thermo-kinetic desorption effects.

BACKGROUND

Chemical vapor detection systems relying on point-sensors are of practical importance because of their potential for excellent performance with small size, low power, and low cost, a combination that is highly desirable for various hand-held and autonomous applications.

One main class of such systems is chemielectric in nature and functions by incorporating an electrically contacted transduction layer that undergoes a change in some electrical property (e.g., resistance or capacitance) in response to the sorption and desorption of the chemical vapor. Examples of materials used in this role include films formed of monolayer-encapsulated gold nanoclusters (metal-insulator-metal ensemble, or MIME), single-walled carbon nanotubes (CNT), graphene, and reduced graphene oxide (rGO), and the recently developed trilayer films of transition metal dichalcogenides (TMD). See Arthur W. Snow, F. Keith Perkins, Mario G. Ancona, Jeremy T. Robinson, Eric S. Snow, and Edward E. Foos, "Disordered Nanomaterials for Chemielectric Vapor Sensing: A Review," *IEEE Sensors Journal*, Vol. 15, No. 3, March 2015, pp. 1301-1320.

The temperature-dependent desorption of a vapor from a solid surface in vacuum is a phenomenon used by an analytical technique known as thermal desorption spectroscopy (TDS) or temperature programmed desorption (TPD) to investigate surface chemical interactions. See P. A. Redhead, "Thermal desorption of gases," Vacuum 12, 203 (1962). For analysis purposes, TDS is generally used on carefully prepared homogeneous surfaces and is done in ultra-high vacuum so that no adsorption or re-adsorption occurs during the measurement and mass spectrometry may be used.

In this technique, a mass spectrometer is used to monitor desorption of molecules from an initially very cold substrate as its temperature is raised, with inferences regarding the detailed chemical interactions at the surface being drawn from the results. Measurements using this technique are typically taken at temperatures well below room temperature.

FIG. 1A shows the results of measurements taken using this technique for detection of various organic compounds on carbon nanotubes, while FIG. 1B shows the results of measurements (in arbitrary units) taken for desorption rate of deuterated water from two organic functional group surfaces (—COOH and —CH$_3$) after different levels of exposure to water vapor. The table shows calculated desorption energies E$_d$ for water from surfaces comprising the listed chemical functional groups. See J. Goering, E. Kadossov, and U. Burghaus, "Adsorption kinetics of alcohols on single-wall carbon nanotubes: An ultrahigh vacuum surface chemistry study," *J. Phys. Chem. C* 112, 10114 (2008) (carbon nanotubes); and R. L. Grimm, N. M. Ballentine, C. Knox, and J. C. Hemminger, "D$_2$O water interaction with mixed alkane thiol monolayers of tuned hydrophobic and hydrophilic character," *J. Phys. Chem. C* 112, 890 (2008) (water desorption v. temperature, —CH$_3$ and —COOH surfaces) and L. H. Dubois, B. R. Zegarski, and R. G. Nuzzo, "Fundamental studies of microscopic wetting on organic surfaces. 2. Interaction of secondary adsorbates with chemically textured organic monolayers," *J. Am. Chem. Soc.* 112 570 (1990) (organic monolayers).

Another approach to chemical vapor point-sensor systems has been developed by Stephen Semancik and his group at the National Institute of Standards and Technology (NIST) in the area of metal oxide sensors. These type of sensors are widely used, for example, the sensors available commercially from Figaro USA, Inc., and rely on a modulation of the grain boundary electrical resistance of materials like SnO$_2$ or ZrO$_2$ that occurs upon exposure to gas vapors (O$_2$, CO$_x$, NO$_x$) at high temperature (500-800° C.). They also induce the oxidative decomposition of the detected vapor. The original innovation of the NIST group was to combine the metal oxide sensors with microhotplates in order to greatly reduce the electrical power needed to provide the high temperatures. See J. S. Suehle, R. E. Cavicchi, M. Gaitan, and S. Semancik, "Tin oxide gas sensor fabricated using CMOS micro-hotplates and in-situ processing," *IEEE Elect. Dev. Lett.* 14, 118 (1993). Since then he and his group have exploited the temperature control offered by the microhotplate plus computer learning algorithms to enhance both selectivity and response time. See B. Raman, R. Shenoy, D. C. Meier, K. D. Benkstein, C. Mungle, and S. Semancik, "Detecting and recognizing chemical targets in untrained backgrounds with temperature programmed sensors," *IEEE Sensors J.* 12, 3238 (2012); and A. Vergara, K. D. Benkstein, C. B. Montgomery, and S. Semancik, "Demonstration of fast and accurate discrimination and quantification of chemically similar species utilizing a single cross-selective chemiresistor," *Anal. Chem.* 86, 6753 (2014).

A further approach is that of Thomas Thundat and his co-workers at Oak Ridge National Laboratories, who use microfabricated bridges to detect explosive molecules by calorimetry. See L. R. Senesac, D. Yi, A. Greve, J. H. Hales, Z. J. Davis, D. M. Nicholson, A. Boisen, and T. Thundat, "Micro-differential thermal analysis detection of adsorbed explosive molecules using microfabricated bridges," *Rev. Sci. Instr.* 80, 035102 (2009).

Although the "dream" for such sensors is to achieve a dog-like olfactory acuity and form factor, their actual performance is very limited, especially with regard to selectivity, i.e., their ability to discriminate between the target vapor(s) and other atmospheric constituents. For this reason, except for a few analyte-specific implementations such as the conjugated polymer-based chemical sensors produced by Swager and co-workers or the FIDO® chemical sensors produced by FLIR Systems, Inc., chemielectric sensors are never used alone, but instead are almost always combined in an array format with each sensor in the array having a different (and hopefully "orthogonal") response spectrum. The idea is then to use software (often referred to as "chemometrics") to combine the outputs and improve selectivity, even in an environment cluttered with multiple vapors. See J. W. Grate and B. M. Wise, "A Method for Chemometric Classification of Unknown Vapors from the Responses of an Array of Volume-Transducing Sensors," *Anal. Chem.* 2001, 73, 2239-2244.

A second important selectivity strategy often implemented in conventional point-detection systems for chemical vapors is a micro-gas-chromatograph (μGC), together with a pump and a standard-air supply in order to provide the needed discrimination. See S. Zampolli, I. Elmi, F. Mancarella, P. Betti, E. Dalcanale, G. C. Cardinali, and M. Severi, "Real-time monitoring of sub-ppb concentrations of aromatic volatiles with a MEMS-enabled miniaturized gas-chromatograph," *Sensors and Actuators B* 141 (2009) 322-328.

For many vapors of interest, not only is selectivity an issue, but so is the insufficiency of chemielectric sensor sensitivity. To enhance performance in this regard, a preconcentrator is often added to the system, where the preconcentrator collects vapor over an extended period of time and then releases it (via a thermal pulse) abruptly onto the µGC/sensor. See I. Voiculescu, M. Zaghloul, and N. Narasimhan, "Microfabricated chemical preconcentrators for gas-phase microanalytical detection systems," *Trends in Analytical Chemistry*, Vol. 27, No. 4, 2008, pp. 327-343.

Given all of these additions needed to improve performance, a conventional chemical vapor sensor apparatus will typically include the chemielectric sensor itself plus a source of scrubbed air, an air sampling device, a preconcentrator, a micro gas chromatograph, and a micropump. Each of these additions adds to the system complexity, size, power, and cost. This tradeoff is unfortunate in that the improvements come only through degrading the very qualities that are supposed to recommend a point-sensor approach.

An important operational issue regarding the conventional chemielectric point sensor approach is that it invariably involves taking a difference between two measurements, one taken prior to vapor exposure (or often upon exposure to scrubbed air) and the other during vapor exposure. A critical implication of this fact is that the measurement time for conventional chemielectric point sensor systems is set by sorption-desorption kinetics, by the sensor enclosure dead volume, and by fluid flow times that are on the order of seconds or larger. This forces the operation to be quasi-dc (i.e., very low frequency) and that implies that the relevant noise floor is electrical 1/f noise and/or drift which tends to be large (and always much bigger than "chemical noise"). And since the sensitivity is set by a signal-to-noise ratio, it is the 1/f noise floor that ultimately limits the sensitivity of the conventional systems. See Snow et al., supra; see also W. Kruppa, M. G. Ancona, R. W. Rendell, A. W. Snow, E. E. Foos, and R. Bass, "Electrical noise in gold nanocluster sensors," *Applied Physics Letters* 88, 053120 (2006).

SUMMARY

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter. Instead, it is merely presented as a brief overview of the subject matter described and claimed herein.

The present disclosure provides chemielectric sensor systems having both increased sensitivity and increased selectivity. In addition, the sensor systems in accordance with the present invention represent an improvement over prior art sensor systems in terms of their smaller size, lighter weight, greater power, and lower cost, and may become useful in a much broader range of applications.

A chemielectric sensor system in accordance with the present disclosure can include a sensor apparatus and a method for chemical sensing using that apparatus. A sensor apparatus that can be used in the sensor system in accordance with the present disclosure can include a sensor/heater assembly, where the sensor is a chemielectric sensor whose resistivity changes both with a change in its temperature and its exposure to a chemical analyte, and further can include control and analysis electronics which provide electrical power to the sensor for read-out and to the heater to generate the thermal pulses. The resistance transients induced by the latter encode thermokinetic information from which the chemical make-up of the sampled ambient atmosphere can be inferred.

In accordance with the present invention, the heater applies one or more thermal pulses to the sensor to quickly raise its temperature. After the pulse ends, the change in the resistivity of the chemielectric sensor is monitored and analyzed as a function of time. This change in resistivity is indicative of the presence of an analyte on the surface of the sensor.

Measurements of the sensor response as functions of the thermal pulse amplitude and of its duration are obtained, and from analyzing these "spectra," improved selectivity, including better estimates for the composition and concentrations of the vapor mixture passing over the sensor element, can be achieved. In addition, the speed of the thermal pulses applied in accordance with the present invention allows higher frequency sensor measurements to be obtained, which enables the sensor system in accordance with the present invention to exhibit lower noise (i.e., as one operates further from the 1/f noise floor), an improved signal-to-noise ratio, and higher sensitivity.

In an exemplary embodiment, the sensor/heater assembly can be situated on a micro air bridge, where the assembly includes a chemielectric sensor element disposed on a heater element that is isolated within and supported by an insulating air bridge material, with the entire assembly isolated from a substrate by an air gap.

In another exemplary embodiment, the sensor/heater assembly can be in the form of a solid multilayer system without the use of an air bridge, where the sensor/heater assembly comprises a chemielectric sensor disposed on an electrically insulating but thermally conducting layer which is disposed on an electrically and thermally insulating substrate. Heat is provided by a resistive heater wire situated between the insulating layer and the substrate, where the heater wire is contacted to a power source configured to apply bias voltage pulses V to the heater wire. Because the wire is separated from the sensor by the electrically insulating but thermally conducting layer, while the electrical properties of the sensor material will not be changed by the application of the voltage V, its temperature will be changed.

Another exemplary embodiment combines aspects from the previous embodiments, and puts a single element that functions both as sensor and heater directly on top of an electrically and thermally insulating substrate. This embodiment includes a chemielectric sensor element mounted on the substrate, where the sensor element is contacted by electrical contacts which provide the bias V to the sensor element. This bias is sufficiently high so that significant Joule heating of the sensor element can occur. At the end of the thermal pulse, the high bias driving the heater current is turned off, but a small measurement bias is left on and it is used to measure the sensor resistance by monitoring the current flow.

In still other embodiments, using any of the configurations described above, multiple sensors are heated by a single heater. Having multiple sensors can be advantageous both for redundancy purposes and to allow a sensor approach to be implemented with different sensors having different coatings or even using different technologies in the interest of further improving selectivity.

The present invention thus also provides methods for improving the sensitivity and selectivity of chemielectric point-sensors while also greatly simplifying the detector system design and lowering its size, weight, power and cost. This new methodology is fairly general in that it may be broadly applied to many different kinds of chemielectric sensors including both chemiresistive and chemicapacitive types.

DETAILED DESCRIPTION

Figure 1A:
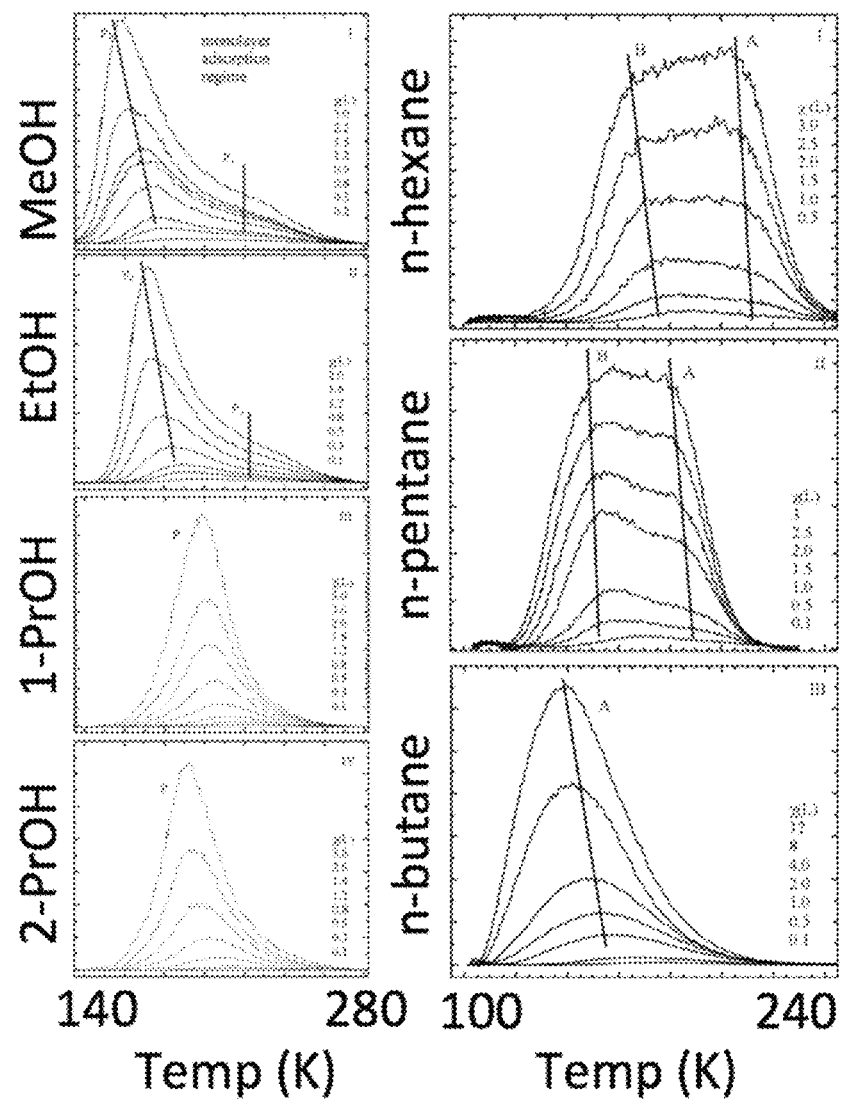
FIGS. 1A and 1B illustrate aspects of the thermal desorption spectroscopy method known in the art for analyzing the temperature-dependent desorption of vapor from a solid surface.
Figure 1B:
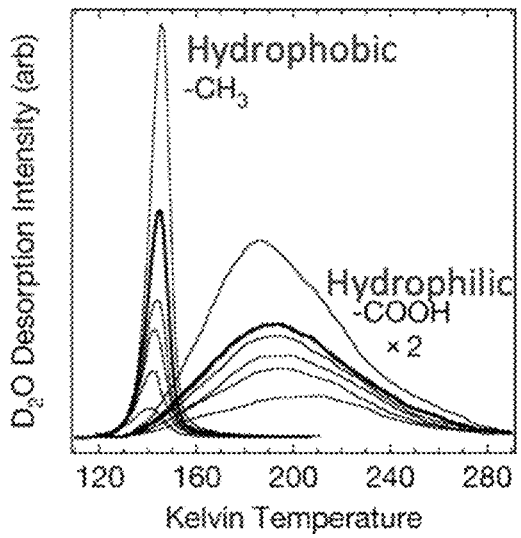

The aspects and features of the present invention summarized above can be embodied in various forms. The following description shows, by way of illustration, combinations and configurations in which the aspects and features can be put into practice. It is understood that the described aspects, features, and/or embodiments are merely examples, and that one skilled in the art may utilize other aspects, features, and/or embodiments or make structural and functional modifications without departing from the scope of the present disclosure.

The present disclosure provides chemielectric sensor systems having both increased sensitivity and increased selectivity. In addition, the sensor systems in accordance with the present invention represent an improvement over prior art sensor systems in terms of their smaller size, lighter weight, greater power, and lower cost, and may become useful in a much broader range of applications.

A chemielectric sensor system in accordance with the present disclosure can include a sensor apparatus and a method for chemical sensing using that apparatus. A sensor apparatus that can be used in the sensor system in accordance with the present disclosure can include a sensor/heater assembly, where the sensor is a chemielectric sensor whose resistivity changes both with a change in its temperature and its exposure to a chemical analyte, and further can include control and analysis electronics which provide electrical power to the sensor for read-out and to the heater to generate the thermal pulses. The resistance transients induced by the latter encode thermokinetic information from which the chemical make-up of the sampled ambient atmosphere can be inferred.

Thus, the present invention provides a way of configuring a chemielectric vapor point-sensor in order to operate at higher speeds, thereby improving its performance in terms of both selectivity and sensitivity. With these enhancements, the advantages point sensors have in small size, weight, power, and cost may become useful in a much broader range of applications.

The chemiresistive sensors described here exhibit a conductivity that varies with the number of molecules condensed onto the surface (or in the case of MIME sensors, diffused into the deposited layer of Au nanoclusters) and interacting with it (or them). This interaction can affect the conductivity through several different mechanisms. See, e.g., N. M. Vörös, R. Patakfalvi, and I. Dékány, "Alkylthiol-functionalized gold nanoparticles for sensing organic vapours: The connection between the adsorption isotherm and the sensor resistance," *Coll. and Surf. A: Physicochem. and Eng. Aspects* 329 (2008), 205-211. The number of condensed molecules on a surface is a function of the ambient concentration of a particular molecule and the nature of the adsorbate/adsorbent pair. This can be described by one of various isotherm models. See, e.g., K. Y. Foo and B. H. Hameed, "Insights into the modeling of adsorption isotherm systems," *Chemical Eng. Journ.* 156, 2 (2010).

These characteristic interaction times are functions of temperature. Thus, in a static equilibrium, the number of adsorbed molecules is a function of the temperature, and in a dynamic equilibrium, the rate of response or recovery after a change in ambient is related to the adsorbate/adsorbent interaction. In the case of the MIME sensor, the diffusion of the analyte through the cluster film is often the rate-limiter on response/recovery. See M. G. Ancona, A. W. Snow, F. K. Perkins, B. Pate, and D. Park, "Analyte kinetics in a nanocluster-based chemiresistor: A case study," *Sensors & Actuators B* 177, 936-946 (2013).

When vapor in the ambient adsorbs to a chemielectric sensor it is transduced into an electrical response that serves as the basic sensing mechanism. When the sensor is joined with a heater to form a sensor/heater assembly, the temperature of the sensor can be pulsed rapidly and controllably, thereby inducing a controllable temperature-dependent desorption. Following the application and removal of a thermal pulse, the temperature of the sensor rapidly rises and then returns to that of the ambient, and the difference in electrical response, e.g., resistance, observed before and after the pulse (with both measurements made at ambient temperature) represents the output signal. The value of this output signal will depend on the temperature reached as a result of the pulse, the duration at which the sensor was held at the elevated temperature, and the particular analytes/interferents contained in the ambient air. By sweeping over the temperature-time space one can form spectra that can be analyzed to distinguish the different analytes and interferents present and also to estimate their concentrations by comparing with control experiments in which only a single vapor is present at a given time.

The present invention thus also provides a way of improving the selectivity and sensitivity of chemielectric point-sensors while also greatly simplifying the detector system design and lowering its size, weight, power and cost. This new methodology is fairly general in that it may be broadly applied to many different kinds of chemielectric sensors including both chemiresistive and chemicapacitive types.

The methodology for operating a chemielectric sensor/heater apparatus described herein can be used to improve the selectivity of chemielectric point sensors by exploiting thermokinetic information. This methodology includes:

(a) Adsorbing molecules present either in individual test vapors (with a single known constituent of known concentration) or in the ambient air (with a mixture of unknown constituents with unknown concentrations) onto the sensor;

(b) Imposing thermal pulses of controlled temperature and duration on the sensor in order to produce the selective and possibly kinetically limited desorption of the sorbed analytes with, for example, more volatile vapors desorbing more quickly and at lower temperatures;

(c) Gathering thermokinetic information about the desorption by measuring the response of the chemielectric sensor, e.g., its resistance, both before and after the thermal pulse (with the sensor at room temperature in both cases) and forming the difference;

(d) Mapping out the space of such sensor responses as a function of both the pulse temperature and its duration with possible focus on particular regions of temperature and durations that are particularly effective at differentiating certain analytes;

(e) Gathering such maps of measured response data (over pulse temperature and duration) for a variety of individual test vapors in the laboratory to form a labeled training set; and (f) Gathering such a map of the ambient air and using machine learning and/or regression techniques to infer which vapors are present in the ambient air and in what concentrations.

In other aspects, the methodology for operating a chemielectric sensor/heater apparatus described herein can be used to improve the sensitivity of chemielectric point sensors by exploiting thermokinetic information, where this methodology includes the following features:

(a) Adsorbing molecules present in the ambient air onto the sensor;

(b) Imposing short thermal pulses of controlled temperature on the sensor in order to produce a rapid desorption of the sorbed analytes; and (c) Gathering information about the desorption by measuring the response of the chemielectric sensor, e.g., its resistance, both before and after the thermal pulse (with the sensor at room temperature in both cases) and forming the difference with the time delay between the two measurements being shorter than about 10 ms so that the relevant noise floor is much lower as it is at a frequency greater than 100 Hz and away from the large 1/f noise that typically limits sensitivity of chemielectric sensors.

In still other aspects, the methodology for operating a chemielectric sensor/heater apparatus described herein can be used to improve the detection of analytes by chemielectric point sensors by exploiting thermokinetic information, where a series of thermal pulses are applied to the sensor element and can be adjusted to the desorption characteristics of a specified analyte, and an electric response of said sensor element is monitored. In accordance with this aspect, the methodology includes the steps of:

(1) defining a specific analyte or mixture of analytes containing said specific analyte;

(2) developing a patterned series thermal pulses for the specific analyte or mixture of analytes wherein frequency, intensity, and duration of the pulses is specified; and (3) conducting a series of sensor response measurements wherein the sensor element is initially in an inert atmosphere, then is exposed to atmosphere being sampled for specified analyte(s) for a defined duration of time, and finally is subjected to the prescribed patterned series of thermal pulses for specific detection of the specified analyte(s).

These sensor element response measurements to the inert atmosphere, to the sampled atmosphere and to the patterned thermal pulses can be repeated at a frequency to conform with an air monitoring requirement.

One advantage in detection of analytes using the chemielectric sensor apparatus in accordance with the present disclosure comes from the "high-speed" characteristics of the sensors in accordance with the present invention, which in the context of the present invention means frequencies of about 100 Hz or higher. The sensing speed for a chemielectric sensor in accordance with the present invention is limited by how fast the temperature of the sensor element can be raised to a predetermined temperature by the applied thermal pulse, how long it is held at that temperature, and then how quickly it can recover back the ambient temperature following the pulse. Of these, the cool-down time is most limiting and is set by the thermal time constant of the chemielectric sensor element, i.e., the time required for the temperature of the sensor element to change by a specified percentage of the total difference between its initial and final temperature when subjected to a step change in applied heating.

Thus, in accordance with the present invention, the sensor apparatus includes a heater element configured to apply a predetermined plurality of thermal pulses to the sensor element, each of the thermal pulses being configured to heat the sensor element to a corresponding predetermined temperature $T_i$, wherein the thermal pulses are applied to the sensor element at a predetermined frequency $f_p$, a time between each of the thermal pulses being greater than the sum of (a) a time needed for the sensor element to reach a predetermined temperature, (b) a time at which the sensor element remains at the predetermined temperature after the application of each pulse, and (c) a time needed for the sensor element to return to a predetermined baseline temperature, where the thermal pulses cause the sorbed analyte to desorb from the surface of the sensor element.

With the application of each thermal pulse, a certain resistance transient follows due to the effects on the chemiresistor of the temperature itself and of the analyte desorption. After the pulse ends and the temperature recovers, the temperature effect on resistance disappears and one is left only with a contribution from the desorption that is then recorded. With the next thermal pulse, the temperature again rises and a new change in resistance is recorded, where the change in resistance arises from any desorption occurring during that pulse. As the pulses continue with increasing temperatures, analytes having a stronger sorption interaction with the sensor and less volatility will come off, causing a further change in the resistance, until all of the sorbed analytes are gone from the sensor surface, at which point no further resistance changes will be observed. The changes in resistance over the series of thermal pulses applied to the sensor element can be analyzed, wherein a specified pattern in a spectrum of values of resistance changes is indicative of a specified analyte in the atmosphere, while the magnitude of that pattern is a measure of the concentration of that analyte. The controlling processor would therefore have to perform a decomposition of the spectrum into its contributing patterns based on single-vapor control experiments.

While some sensor elements may not be suitable for use as the chemielectric sensor of the present invention, e.g., those configured as a thick film or having a long diffusion time, see Ancona et al., supra, many other different types of chemielectric sensor elements can be used in a sensing device in accordance with the present disclosure, including monolayer films (e.g., graphene, $MoS_2$, etc.) and those based on disordered aggregates of nanoelectronic materials (e.g., gold nanoparticles, carbon nanotubes, graphene nanoplatelets, etc.). See Snow et al., supra.

Figure 2:
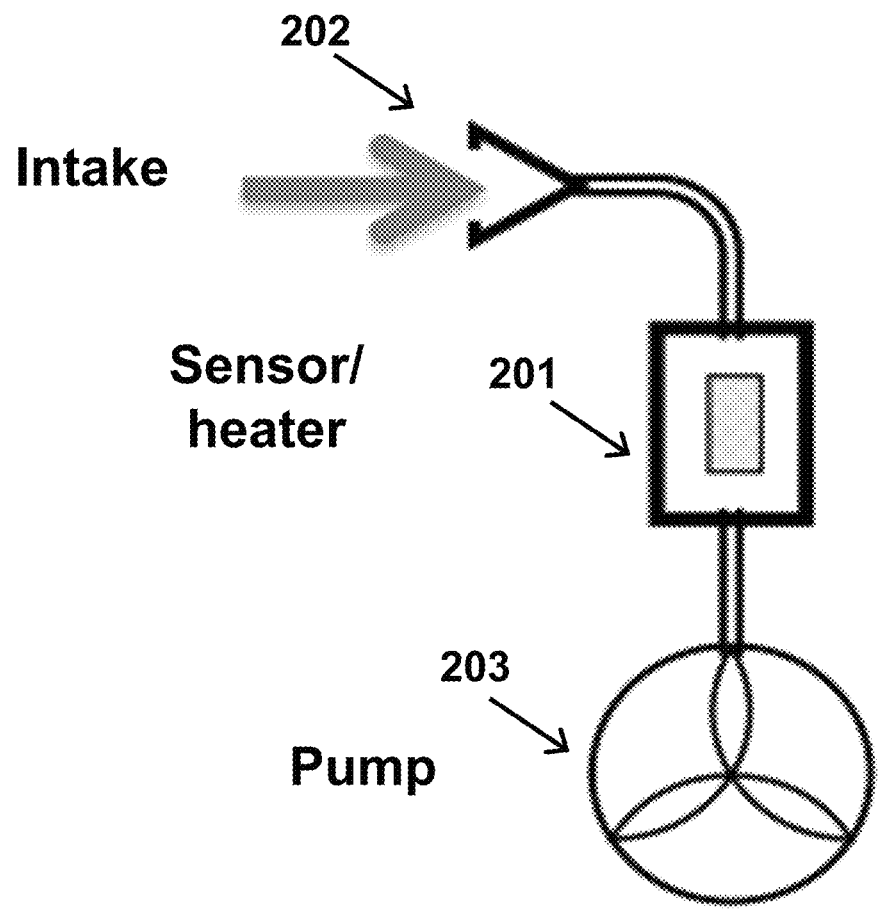
FIG. 2 is a block schematic illustrating aspects of a chemielectric sensor system in accordance with aspects of the present disclosure.

The block schematic shown in FIG. 2 illustrates aspects of the components embodied in a chemielectric sensor apparatus for use in a sensor system in accordance with the present invention. As illustrated in FIG. 2, an exemplary chemielectric sensor apparatus in accordance with the present invention includes a sensor/heater assembly 201, an intake 202, and a pump 203. Pump 203 pulls air (which may contain the analyte(s) of interest as well as multiple potential interferents) from the ambient through the intake 202 and passes it through the sensor/heater assembly 201 for analysis. Purging of the sensor to bring it back to its initial state is accomplished simply by running the pump with the sensor at its maximum temperature.

The sensor apparatus further includes control and analysis electronics (not shown), which provide electrical power to the device and means, e.g., a resistance meter or a capacitance meter, for measuring and processing information regarding an electrical change in the sensor following its exposure to an analyte-containing atmosphere. Thus, exemplary sensor control and analysis components might include a resistance meter wherein an electrical resistance is determined by measuring a current that passes across the sensor device when a particular voltage is applied across it, with the so-calculated resistance is presented as digital information to a, computer (e.g., a co-located processor board such as a Raspberry Pi) where the relationship between resistance, temperature, and thermal history for a particular sensor may be informative in identifying one or more analytes in a gas incident on the sensor.

One skilled in the art will readily appreciate that other embodiments and configurations are possible, and all such alternative embodiments and configurations are deemed to be within the scope and spirit of the present disclosure.

For example, in some embodiments, pump 203 is omitted, with the air flow being driven instead by the motion of the platform on which the system is situated, such as a moving drone. Other embodiments might include multiple sensor/heater assemblies 201, either for redundancy or where the type of sensor used is different and allows for better coverage of the thermokinetic and chemical space. As would be readily appreciated by one skilled in the art, such a sensor system in accordance with the present invention is much simpler, smaller, and less expensive than conventional chemical point-sensors which require an additional scrubbed air supply, preconcentrator, and microgas-chromatograph.

The presence of vapor molecules adsorbed onto the point sensor is detected by the sensor's ability to transduce a chemical signal to an electrical one. Most commonly the latter is a change in transducer film resistance that is detected by applying a voltage and monitoring the change in current. Gathering similar data during rapid thermal pulsing of the sensor constitutes the basic operation of the present invention.

Figure 3:
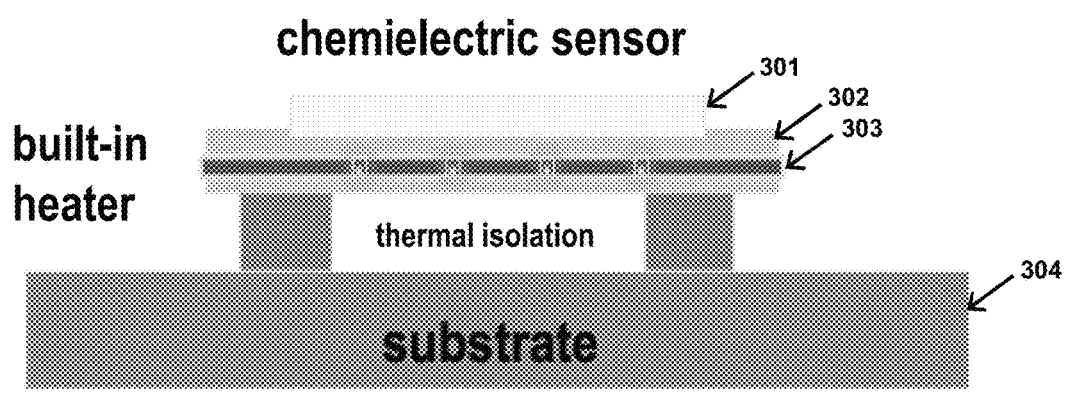
FIG. 3 is a block schematic illustrating aspects of a first exemplary embodiment of a chemielectric sensor system in accordance with aspects of the present disclosure.
Figure 4:
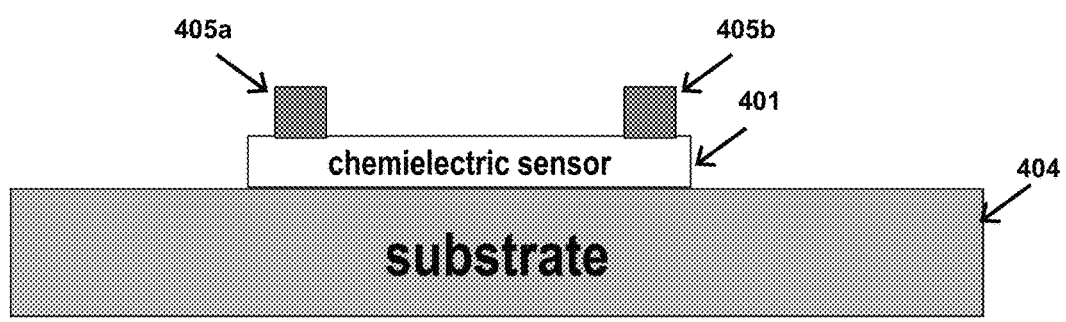
FIG. 4 is a block schematic illustrating aspects of a second exemplary embodiment of a chemielectric sensor system in accordance with aspects of the present disclosure.
Figure 5:
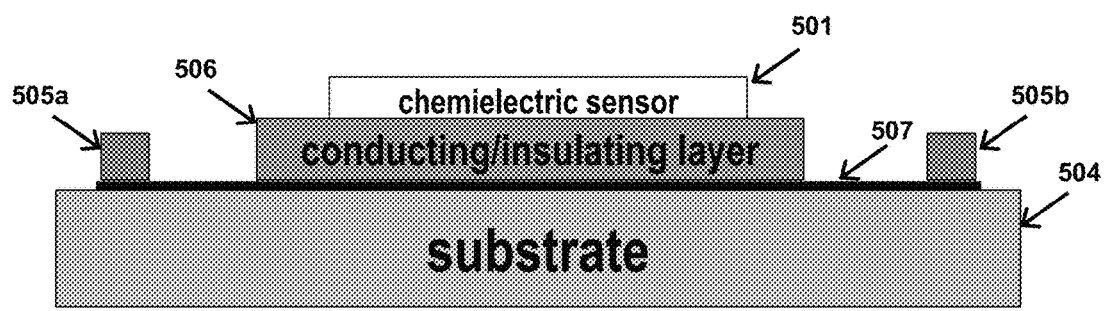
FIG. 5 is a block schematic illustrating aspects of a third exemplary embodiment of a chemielectric sensor system in accordance with aspects of the present disclosure.

FIGS. 3, 4, and 5 illustrate three exemplary embodiments of a chemical sensor/heater assembly that can be incorporated into a chemielectric sensor system in accordance with the present invention.

FIG. 3 illustrates aspects of a first exemplary embodiment of such a chemical sensor/heater assembly. A key feature of this embodiment of the sensor/heater assembly is that sensor and heater are thermally well isolated from other components in the sensor system. The reason for the isolation is simply to reduce the amount of material being heated so that less energy is required to increase the temperature by the desired amounts, which in turn lowers the power requirements of the sensor system. This is important because a point sensor is generally of little value unless it can be small in size and in energy consumption. It should also be noted that although the isolation slows the thermal response of the sensor/heater assembly, as discussed below with respect to FIG. 7, it does not slow the response so much that the function of the high-bandwidth detector is compromised (i.e., the thermal time constant is still below 1 msec).

Thus, as illustrated in FIG. 3, one embodiment of a sensor/heater assembly for use in a chemielectric sensor system in accordance with the present invention can include a chemielectric sensor element 301 disposed on a heater element 303 that is isolated within and supported by an electrically and thermally insulating air bridge material 302, with the entire assembly isolated from the substrate 304 by an air gap 305. This suspended design amounts to creating a micro air bridge, separated from the substrate by an air gap, on which the sensor/heater assembly is situated. The thermal isolation provided by the air gap greatly reduces the energy needed to elevate the sensor temperature, and thus can keep the power requirements of such a sensor system modest.

However, in other embodiments noted below, such an insulating air bridge is not necessary and will not be included.

In most embodiments, sensor element 301 will generally include a transducer material such as, e.g., functionalized gold nanoparticles or carbon nanotube random networks deposited on an insulating substrate (e.g., $SiO_2$) with the sensor element being contacted electrically with patterned metal (e.g., Au), though any suitable chemielectric sensor technology can be employed, such as reduced graphene oxide platelets, graphene films, transition metal dichalcogenide mono- or few-layer films, or some other chemiresistive material such as metal oxide nanostructured materials.

Substrate 304 that supports the suspended structure can be anything that allows the air bridge design to be fabricated, and its properties are otherwise irrelevant. Heater element 303 typically will be simply a metal wire, perhaps patterned in a serpentine shape and heated by a controllable power source, that resides within the air bridge 302, with the air bridge 302 being formed from any suitable insulating material robust enough that it can support the heater element in its given configuration. However, heater element 303 need not be a metal wire, and any suitable material may be used. One simple process for creating the desired structure using microelectronic fabrication methods would be to start with an SOI (silicon-on-insulator) wafer, define the heater element, cover it with an insulator such as deposited silicon nitride that will form the air bridge, define the sensor electrodes, selectively etch away a portion of the underlying $SiO_2$ insulator layer to produce the suspended silicon nitride/buried wire/silicon structure, and finally apply a gold nanocluster film as the transductive material. For embodiments employing multiple sensors (described below) a single air bridge could accommodate all of the sensors thereby simplifying the design.

In this type of design, the power levels needed to get the required temperature rises is no more than about 20-30 mW, with the needed combination of current and voltage, e.g., 20-30V and 1 mA of current, determined by the heater resistance that can be chosen for design purposes simply by selecting the heater wire width/length ratio.

An alternative approach is to situate the sensor/heater assembly directly on a thermally insulating substrate so that the complication of the air bridge is eliminated. In such embodiments, a very low thermal conductivity material like $SiO_2$ or glass or plastic would be suitable as the substrate material. The operation of the sensor/heater assembly would be precisely as before, i.e., the heater is used to pulse the temperature of the sensor briefly and electrical readings are taken before and after the pulse with the sensor signal being formed of their difference. Although this design might consume somewhat more power than the air bridge design due to extra heat loss through the substrate, it would also have a shorter time constant that could be beneficial in increasing bandwidth even further.

An exemplary embodiment of a sensor/heater assembly reflecting this approach is illustrated in FIG. 4. In this embodiment, the sensor/heater assembly is in the form of a solid multilayer system without the use of an air bridge, where the sensor/heater assembly comprises a chemielectric sensor 401 disposed on an electrically insulating but thermally conducting layer 407 which is disposed on an electrically and thermally insulating substrate 404. As in the embodiment described above with respect to FIG. 3, the sensor element can comprise any suitable material such as functionalized gold nanoparticles, carbon nanotube random networks deposited on an insulating substrate, reduced graphene oxide platelets, graphene films, transition metal dichalcogenide mono- or few-layer films, or some other chemiresistive material such as metal oxide nanostructured materials.

The material for layer 407 could be deposited silicon nitride ($Si_3N_4$), silicon oxide ($SiO_2$), aluminum oxide ($Al_2O_3$), or any other suitable material which can be deposited at a temperature consistent with the preexisting materials including the heating element, while substrate 404 could be an $SiO_2$ layer on a silicon chip/wafer. Heat is provided by a resistive heater wire 408 situated between the insulating layer 407 and substrate 404 which is contacted to a power source via electrical contacts 406a/406b, where the power source is configured to apply bias voltage pulses V to the heater wire to produce the Joule heating. Because the wire is separated from sensor 401 by electrically insulating but thermally conducting layer 407, the electrical properties of the sensor material will not be changed by the application of the heater voltage V but its temperature will be changed. In most embodiments, power levels needed to achieve the necessary temperatures in this type of design are roughly 100 mW, with the exact combination of voltage and current, e.g., 30V and 3.3 mA, needed to produce this amount of Joule heating being determined by the heater wire design.

For example, in one implementation of such a structure, layer 404 was 100 nm $SiO_2$ on a Si wafer, the heater wire 408 was formed from a patterned sequential deposition of 2 nm Ti/20 nm Au/2 nm Ti, layer 407 was 150 nm plasma-enhanced chemical vapor deposited $Si_3N_4$, with holes etched to allow contacts 406a and 406b to the heater wire 408, and the chemielectric sensor 401 was formed from a deposited layer of organic functionalized Au nanoparticles. Multiple devices were fabricated, and the typical resistance of the heater wire fell between 125 and 140 Ω. In this case, requisite power levels were rather high, of order 12 W to heat to 55° C. in a sequence of 0.1 s pulses, with amplitude increasing gradually to 40V.

Another exemplary embodiment, aspects of which are illustrated by the block schematic in FIG. 5, combines aspects from the previous embodiments and puts a single element that functions both as sensor and heater directly on an electrically insulating surface of a thermally conducting substrate. The data in FIG. 13 is from a design of this type.

This embodiment includes a chemielectric sensor element mounted on a substrate, where the sensor element is contacted by electrical contacts which provide the bias V to the sensor element. This bias is sufficiently high so that significant Joule heating of the sensor element can occur. At the end of the heat pulse, the high bias driving the heater current is turned off, but a small measurement bias is left on and it is used to measure the sensor resistance by monitoring the current flow.

Such an alternative embodiment can be created if the chemielectric sensor element is capable of carrying sufficient current to heat itself without suffering damage. For example, although this is not possible for a sensor element based on gold nanoparticles, it is possible with a graphene-based sensor, e.g., a sensor formed of a graphene sheet mounted directly on the substrate. In such cases, a separate heater element is not needed.

Thus, in such embodiments, where the sensor element electrical resistance R (which is likely to be temperature dependent, and is certainly ambient exposure dependent), the sensor element can be placed in "heater mode" by application of a large bias voltage V so as to get the desired Joule heating by dissipation of power $P=V^2/R$. Since the sensor and heater are the same material, the heater wire design is no longer arbitrary as in the other embodiments, and typically this implies a lower electrical resistance and hence a lower voltage and higher current than in the previous designs in order to achieve the same amount of Joule heating. At the end of the thermal pulse, to return the sensor element to "sensor mode," the high bias driving the heater current is turned off, with a small predetermined measurement bias being left on, which is used to measure the sensor resistance by monitoring the current flow. Combining the sensor and heater into a single element obviously simplifies the mechanical design significantly. The simplicity of a sensor system in accordance with this embodiment would be especially helpful in the case of multiple sensors discussed below, where the multiple sensors would otherwise demand multiple air bridges each with separate contacts.

An exemplary configuration of a sensor/heater element according to this approach is illustrated by the block schematic in FIG. 5, in which a chemielectric sensor element 501 mounted on substrate 504 is contacted by electrical contacts 506a/506b which provide the bias V to the sensor element.

To apply heat to the sensor element, the bias V is sufficiently high so that significant Joule heating occurs in a manner described above with respect to FIG. 3, causing the temperature of the sensor element to rise as desired to a prescribed temperature, e.g., from about 20° C. to about 180° C. After a prescribed time interval at the desired temperature, the high bias driving the heater current is turned off to end the heat pulse, with a sufficiently small measurement bias being left on which is used to measure the sensor resistance by monitoring the current flow. Crucial to this design is that the substrate have a very low thermal conductivity since otherwise there will be strong heat conduction to the substrate and the power requirements will rise tremendously. Materials with suitably low thermal conductivities are $SiO_2$, glass, and plastic.

Figure 13A:
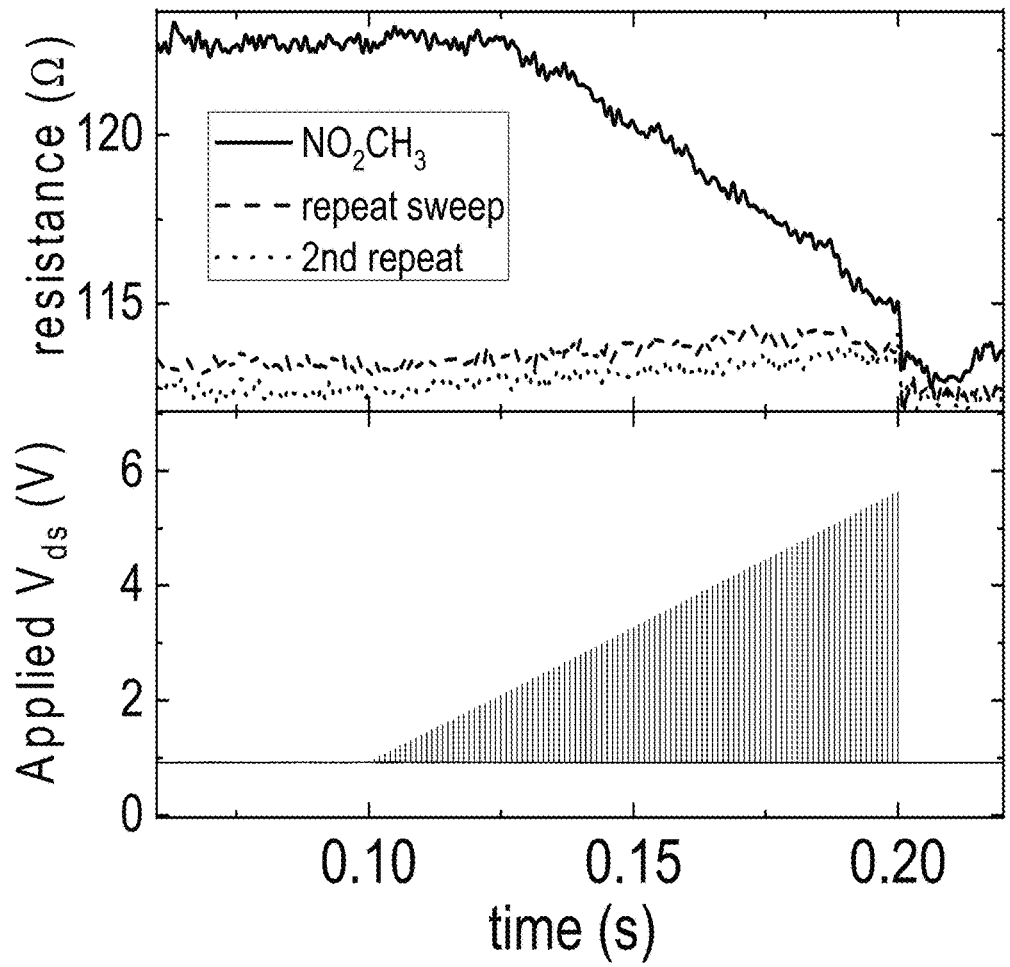
FIGS. 13A-13C are plots illustrating the conductivity of an unmodified graphene film sensor during a series of rapid thermal cycling experiments with exposure to nitromethane, nitrogen dioxide, or nitrotoluene.
Figures 13B, 13C:
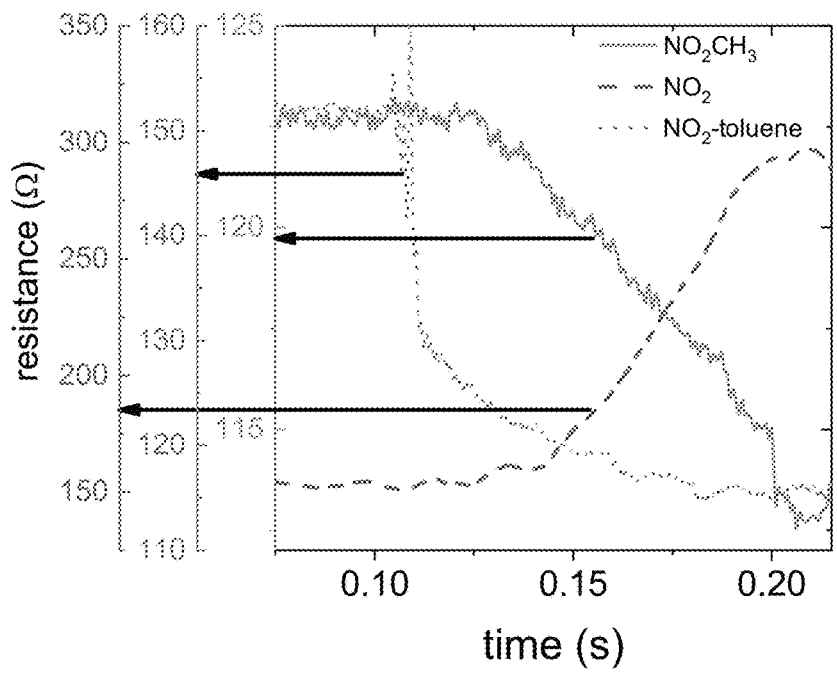

For example, in the particular case illustrated in FIG. 13B, comprising a chemically vapor deposited graphene layer transferred onto a $SiO_2$ film on a Si wafer and fabricated into a two terminal electronic device, with a channel length and width of 4 and 60 µm, respectively, the room temperature resistance R was 114 Ω. In this experiment, after exposing the device to a dilute concentration of nitromethane, the applied bias voltage was swept from 0.9 V ("sensor mode") to 5.6 V ("heater mode") in 101 20 µs pulses over 100 ms. The power level needed at the last pulse to reach the required temperature rise in this experiment (to 180° C.) was 200 mW. The energy dissipated by the device over the 0.2 s duration of this experiment was only 10 nJ.

A further alternative comes from noting that in any of the foregoing designs it is possible to have multiple sensors heated by a single heater. Having multiple sensors can be advantageous both for redundancy purposes and to allow a sensory approach to be implemented with different sensors having different coatings or even using different technologies in the interest of further improving selectivity.

Figure 6:
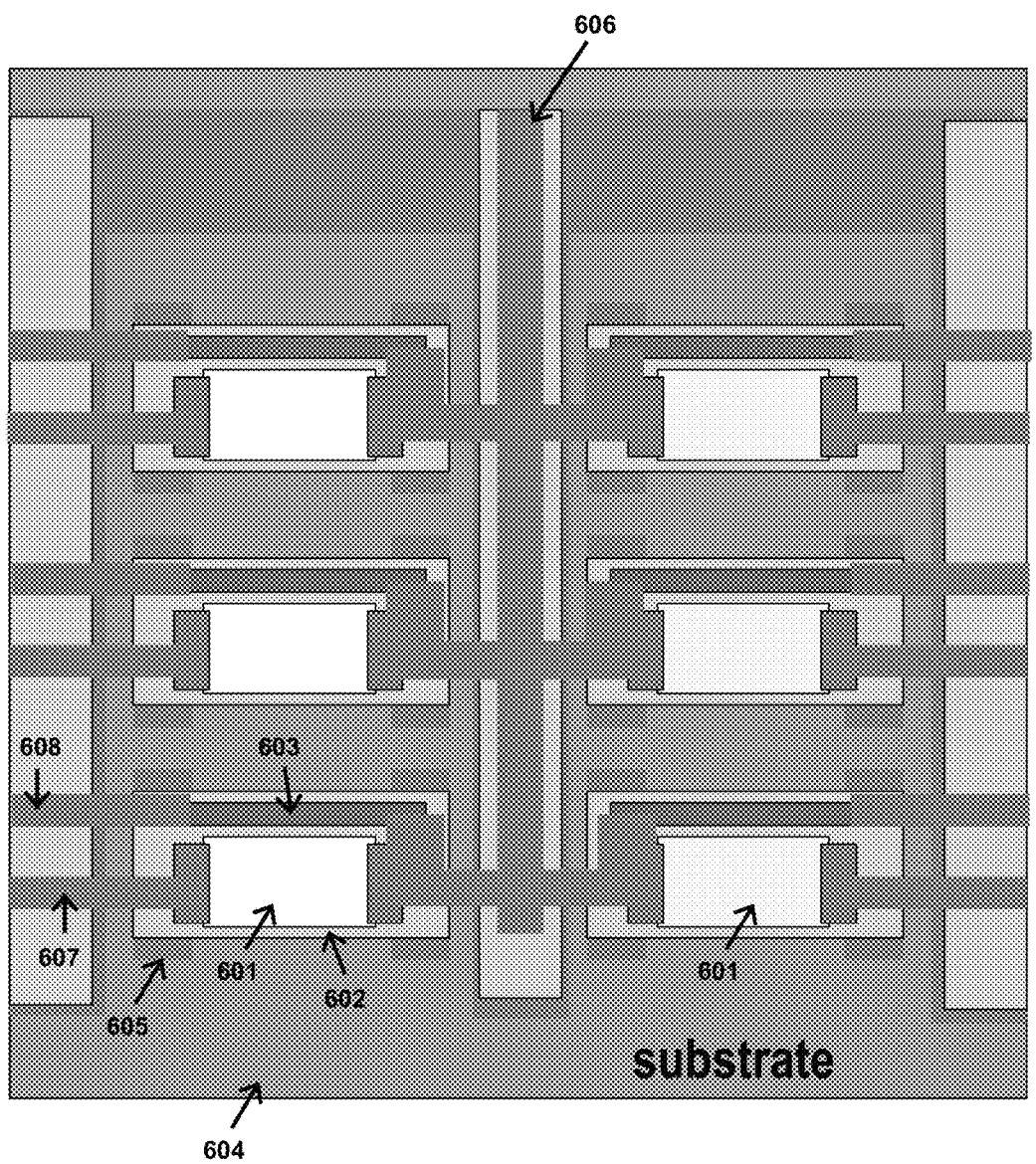
FIG. 6 is a block diagram depicting a further exemplary embodiment of a chemielectric sensor system in accordance with aspects of the present disclosure.

An example of this type of design is depicted in a top view in FIG. 6. In this embodiment there is an array of six sensor/heater assemblies of the suspended type shown in FIG. 3. In the example shown, the chemielectric sensor element 601 of each assembly is disposed adjacent to its heater element 603 and both are supported by and isolated from each other by an insulating air bridge material 602, with the entire assembly isolated from the substrate 604 by an air gap that is created by the bridge support layer 605. All the sensors and heaters are tied to a central ground line 606, and then each sensor and heater have separate connections, e.g., in the bottom level assembly the wire connections are 607 and 608. These connections allow the voltages to be applied to the chemiresistive sensor in order to measure the vapor-induced resistive changes or to the heater in order to produce the Joule heating. In this design, the sensors could be identical for redundancy purposes, or for aid in selectivity could be different types of sensors, e.g., MIME sensors with different chemical functionalizations or a mix of MIME and carbon nanotube sensors.

Figure 7A:
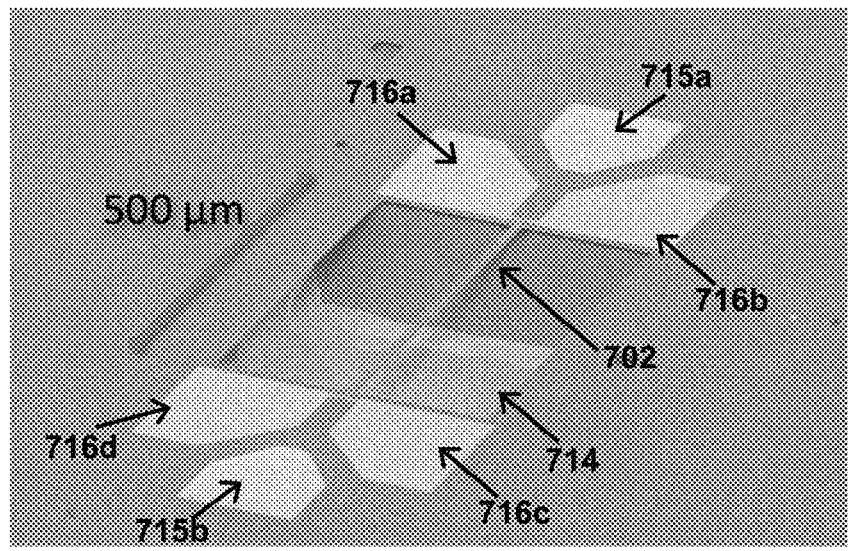
FIGS. 7A and 7B are electron micrograph images illustrating aspects of an exemplary chemielectric sensor system in accordance with aspects of the present disclosure that was reduced to practice by the inventors of the present invention.
Figure 7B:
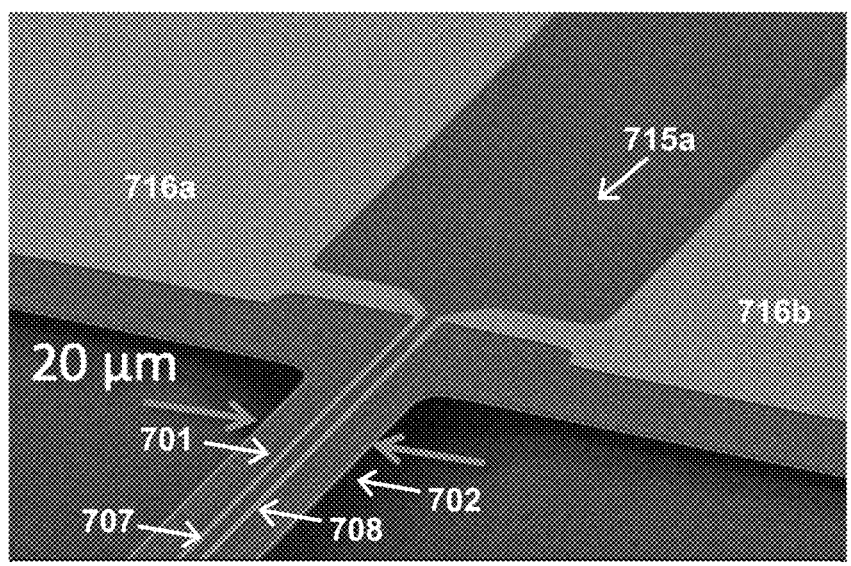

An exemplary device in accordance with the present invention that was fabricated by the inventors of the present invention is illustrated in FIGS. 7A and 7B. This device is of the type depicted in FIG. 3, where the sensor/heater assembly is situated on an air bridge over the substrate.

As shown in the micrograph in FIG. 7A, in this exemplary embodiment, a chemielectric sensor system in accordance with the present invention includes a chemielectric sensor/heater assembly fabricated on an air bridge 702 suspended over a substrate 714. Contact pads 715a/715b provide electrical access to the heater wire and allow voltages/currents to be supplied in order to effect the Joule heating. The sensor in such an embodiment typically will be a MIME sensor (see H. Wohltjen and A. W. Snow, "Colloidal metal-insulator-metal ensemble chemiresistor sensor," *Anal. Chem.* 70 (1998) 947-949) in which the transductive material is formed of functionalized gold nanoclusters deposited on the air bridge 702 and between the electrical leads contacted at either end by means of the contacts 716a-716d, and in this way its vapor-dependent resistance can be measured with reduced sensitivity to the resistance along the fine leads 707, 708. All wires and contacts are made of gold and the air bridge is composed of silicon nitride.

The micrograph in FIG. 7B provides a close-up of a portion of the suspended sensor/heater assembly at one end of the air bridge. As can be seen in FIG. 7B, the sensor/heater assembly includes the two closely spaced wires 707 and 708 connected to electrical contacts 716a/716b, where wires 707/708 contact sensor 701, in this case a gold nanocluster film, that is situated between them so as to monitor its resistance. The heater is not visible in this picture because it is hidden beneath an insulating layer of silicon nitride.

Figure 8:
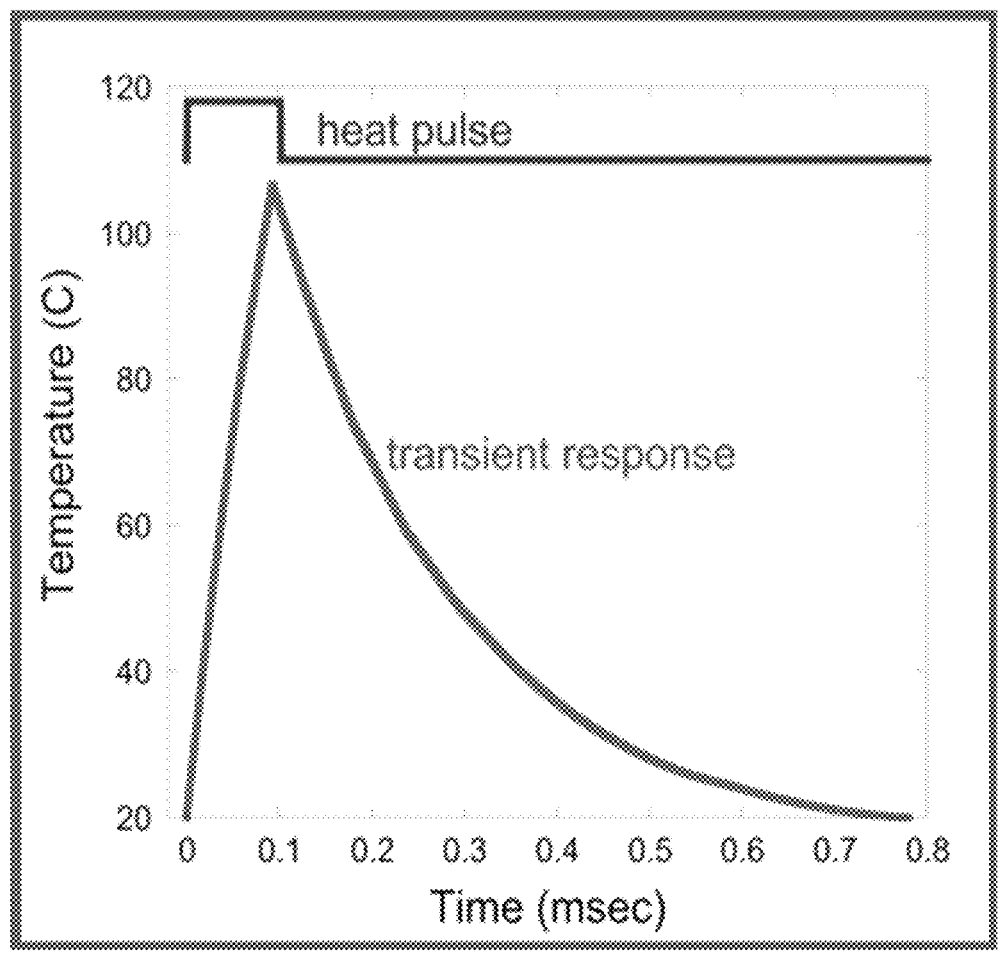
FIG. 8 illustrates aspects of the thermal characteristics of a chemielectric sensor system in accordance with aspects of the present disclosure.

A numerical simulation of the thermal response of the sensor/heater assembly of FIG. 7 to heating by the electrically activated heater wire in an air bridge-based configuration appears in FIG. 8. As shown in FIG. 8, upon the activation of the heater wire to provide a thermal pulse, the temperature of the assembly rises rapidly from about 20° C. to about 105° C., peaks at the end of the thermal pulse, and then cools. From the results shown in the plots in FIG. 8, it can be concluded that in the exemplary case illustrated by FIG. 8, the thermal time constant of the sensor element is about 0.2 msec, which indicates that the air bridge design provides a sensor bandwidth of about 5 kHz.

Figure 9:
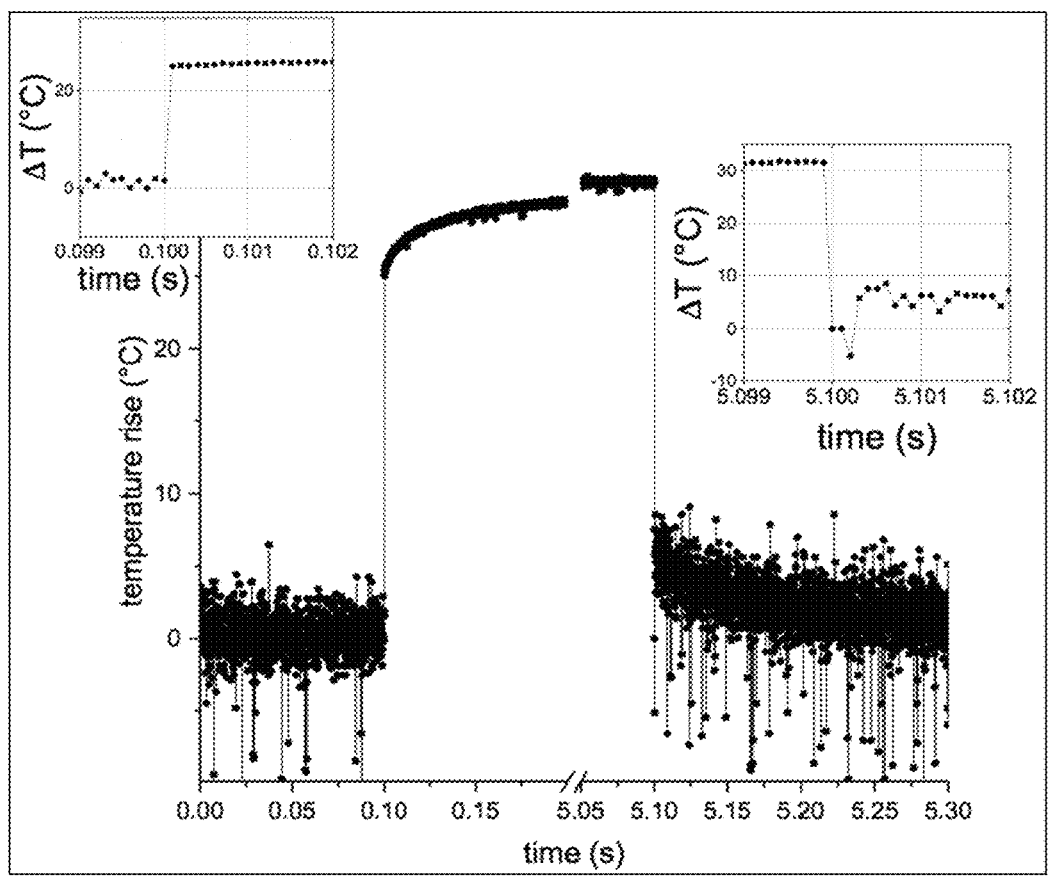
FIG. 9 provides plots showing data taken from an exemplary chemielectric sensor system in accordance with aspects of the present disclosure.

FIG. 9 shows the results of a single experiment carried out with a graphene sensor/heater element configured as in FIG. 5. Having previously carried out a measurement of the electrical resistance of the graphene sensor/heater element as a function of temperature, the inventors were able to calculate the temperature of the graphene sensor/heater element as a function of measured electrical resistance. To do so, they established a steady-state condition in a dry nitrogen ambient in which a small voltage was applied to contacts 505a and 505b (as in FIG. 5), and from the measured current the resistance was calculated and the temperature inferred as plotted in FIG. 9.

The applied voltage was then abruptly increased while the current flowing through the device was continuously sampled at 10 kHz. In this experiment, the temperature was observed to increase by about 30° C. after 5 seconds, but as can be seen from the upper left inset, over 85% of the increase occurred within 100 µs. The applied bias was then abruptly decreased back to the original small level, with the temperature rapidly recovering as well, as shown in the upper right inset.

Consideration of these equilibration rates indicates that operation with short pulses of order 1 msec or less at a relatively high frequency (for vapor sensors) on the order of 100-1000 Hz is possible. This is advantageous in sensors because of the problem of the ubiquitous 1/f noise, which is of course lessened at higher sampling frequencies. See A. A. Balandin, "Low-frequency 1/f noise in graphene devices," *Nature Nanotechnology* 8 (2013), 549-555. According to measurements like those described in Kruppa et al., supra, operation in this fashion should be sufficient to greatly improve the performance of the sensor. Since the minimum detectable level (MDL) of concentration of a molecule by a sensor is determined by the specific response of the sensor to the molecule and the noise level of the sensor, one would like to reduce the noise level as much as possible.

A chemielectric sensor system in accordance with one or more aspects of the present invention can also provide enhanced sensitivity, enabling the detection of chemicals in a vapor at lower concentrations. The limit on sensitivity for a given sensor (or minimum detectable level or MDL) is set by its level of noise in the device as discussed above, and is reached when the signal-to-noise ratio falls below some minimum value. Amplification of the signal is typically not productive because the noise is also amplified, and so lowering the noise floor is usually a better route to improved sensitivity.

As noted in the Background section, in a chemielectric point sensor, the transduced signal that is proportional to the vapor concentration is actually derived from a difference between two measurements, one taken prior to vapor exposure under purging conditions and the other during vapor exposure. In a conventional sensor, these two measurements are necessarily separated by a time delay of at least seconds since the time to switch between a "no vapor" (or scrubbed air) state and a "vapor present" state is limited by the slow sorption equilibration and flow times. Because electrical noise (which at very low frequencies is indistinguishable from "drift") rises inversely with frequency (i.e., 1/f noise as measured, e.g., in Kruppa et al., supra,), it introduces large errors when the time between measurements is seconds (or more). And this represents a large noise floor for the sensor, thus reducing the signal-to-noise ratio, and limiting sensitivity.

Figure 10:
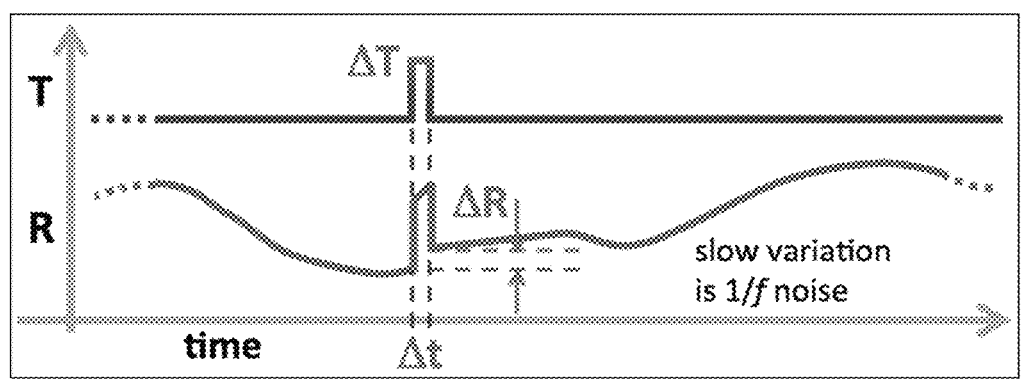
FIG. 10 is a schematic showing heat-pulse generated waveforms and operation used to improve sensitivity in an exemplary chemielectric sensor system in accordance with aspects of the present disclosure.

A high-speed sensor in accordance with the present disclosure, e.g., as depicted in FIGS. 3-6, can overcome this 1/f noise problem, as illustrated by the plot shown in FIG. 10.

The upper trace in FIG. 10 depicts the temperature versus time for a chemielectric sensor, in this case a chemiresistor sensor whose resistance changes upon exposure to a chemical analyte. As described in more detail below, the bottom trace in FIG. 10 depicts the corresponding resistance of the chemiresistor at various times as the temperature changes, where the random variation of the resistance with time reflects the 1/f noise and/or drift of the chemiresistor.

The response and recovery of the temperature of the sensor/heater assembly to a thermal pulse can occur in less than a millisecond, as illustrated by the data shown in FIGS. 8 and 9. So long as chemical diffusion times are not longer than this response/recovery time, the response/recovery time of the sensor/heater assembly to a thermal pulse represents the response time of the sensor. This is also why in FIG. 10, the rise/fall of the thermal pulse and the resulting resistance change are shown as effectively instantaneous. This is much faster than the response time of a conventional sensor (which is on the order of 1 second or longer as already discussed), and consequently, the present invention can be regarded as providing "high-speed" (or "high-bandwidth") chemical sensing.

During the thermal pulse, the temperature of the sensor is rapidly elevated, and the resistance of the sensor changes as a result of both the higher temperature itself and the chemical desorption induced by the higher temperature. When the pulse ends, the temperature quickly drops back to ambient, but the resistance does not drop to its base level because some of the analyte has been desorbed. The difference in resistance $\Delta R$ constitutes the signal, and since the difference $\Delta t$ in measurement times before and after is much smaller than the time scale of the typically large 1/f noise, the noise floor will be much lower, the signal-to-noise ratio much higher, and the sensitivity enhanced.

A chemielectric sensor system in accordance with one or more aspects of the present invention can also provide enhanced selectivity, enabling the detection of a specific analyte of interest in a vapor containing multiple analytes. The selectivity approach of this invention is in principle similar to the thermal desorption spectroscopy (TDS) approach described above, in which vapor components can be identified by the temperature at which desorption onset of the individual components occurs.

To demonstrate that a TDS-like mechanism can work with a chemielectric sensor system in accordance with the present invention which is at atmospheric pressure and near room-temperature, the inventors carried out an experiment with a conventional MIME sensor known in the art and a set of structurally and chemically similar analytes: ethanol (EtOH), dichloropentane (DCP), triethylamine (TEA), butylamine (BuAm), and chloroethyl diethyl amine (Cl-TEA), at a range of concentrations.

A pair of identical MIME sensors that were designed to be particularly sensitive to amines and insensitive to everything else (including relatively reactive species such as DCP and volatile species such as EtOH) were placed on a hot plate under steady state vapor conditions of dilute analyte vapor in dry $N_2$ gas with the resistance monitored while the temperature was slowly raised to about 60° C., held for 10 minutes, and then slowly cooled. The data is presented in FIG. 11 showing the normalized change in conductance $\Delta G/G_0$ over time as the temperature rises for the various analytes.

Figure 11:
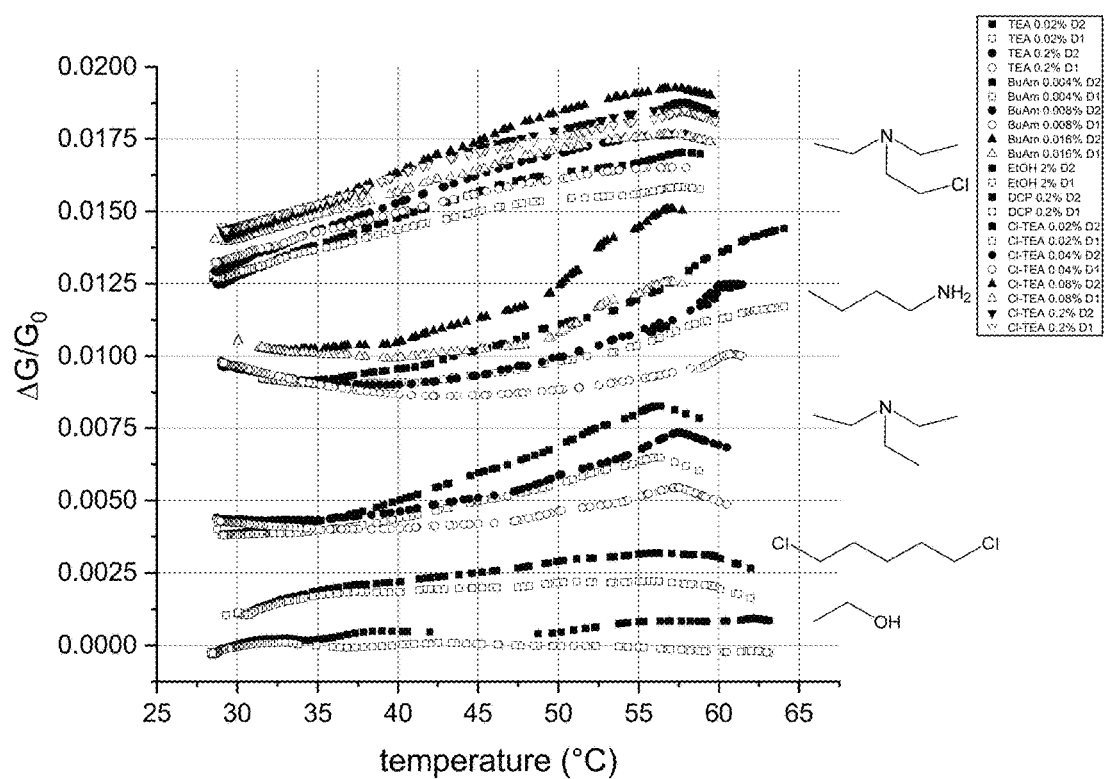
FIG. 11 is a plot showing the conductivity of a pair of metal-insulator-metal ensemble (MIME) sensors as the temperature is slowly raised and lowered in ambients containing different concentrations of five different vapors.

To understand the data of FIG. 11 it is important to note that it was not collected using a sensor/heater assembly in accordance with the present invention. In particular, that fact that fast thermal pulses were not used means that the resistance measurements are made at varying temperatures and so some of the variation seen is that of the sensor itself, and not just that due to the vapor. To account for this, the data in FIG. 11 has had the measured variation in sensor resistance when measured in dry $N_2$ versus temperature subtracted off. Thus, the variations that remain are due to the vapor exposure, and thus FIG. 11 demonstrates that a sensor can have markedly different responses versus temperature for different analytes, which is the fundamental basis for the selectivity in the present invention.

It may be easily seen in FIG. 11 that the qualitative behavior varies significantly among the amines BuAm, TEA, and Cl-TEA, while being remarkably consistent through repeated trials of one analyte, independent of concentration. It may also be observed that two of the compounds investigated in this trial, EtOH and DCP, did not induce a sensor response significantly different from a straight line, particularly between the range of 35° C. and 55° C. However, it should be noted that the alkyl thiol encapsulating layer of the gold nanoclusters employed by this particular MIME sensor incorporated carboxylic acid (—COOH) functional groups. This design was used because of its strong interaction with amines and relative insensitivity to other compounds. Thus it is anticipated that other sensors, by design more or less sensitive to particular moieties or functional groups of molecules, will provide equivalent discrimination among the targeted molecules while generally ignoring the others.

Figure 12A:
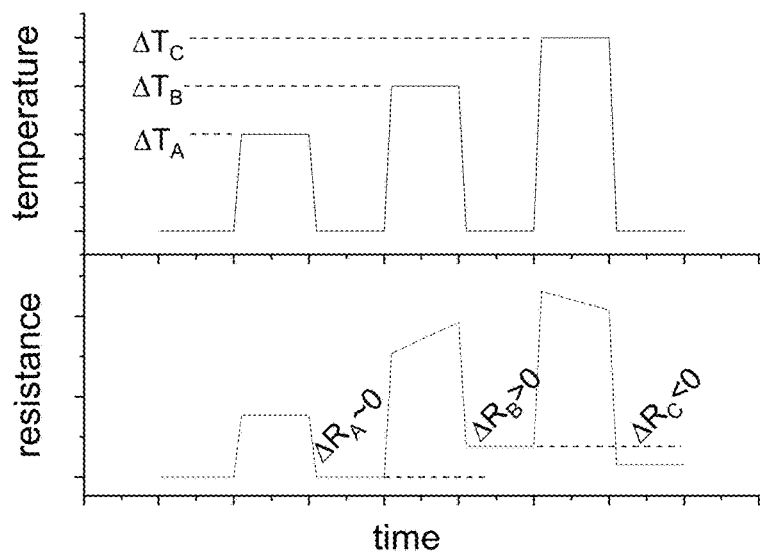
FIGS. 12A and 12B are schematics illustrating heat-pulse generated waveforms and ways in which a chemielectric sensor in accordance with aspects of the present disclosure can be used to identify a specific chemical analyte incident on the sensor.
Figure 12B:
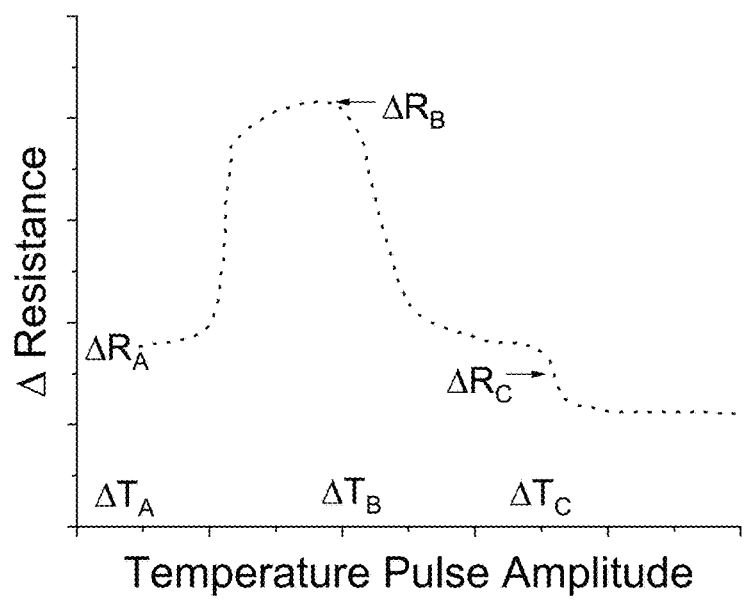

FIGS. 12A and 12B illustrate an exemplary way in which the steady-state behavior of the sensor illustrated by the plots in FIG. 11 can be exploited by a high-speed chemielectric sensor/heater assembly in accordance with the present invention to provide improved selectivity in chemical detection.

In cases where selectivity is desired, thermal pulses are applied to the sensor in the same manner as described above, but in this case, as illustrated in FIG. 12A, a rapid sequence of short thermal pulses is used, with each pulse of a fixed duration increasing the sensor temperature by a fixed amount ΔT over the prior pulse. With the application of each thermal pulse, a certain resistance transient follows due to the effects on the chemiresistor of the temperature itself and of the analyte desorption. After the pulse ends, the temperature effect on resistance disappears and one is left only with a contribution from the desorption that is then recorded, e.g., $\Delta R_A$ in response to a pulse that raises the temperature of the sensor element to temperature $T_A$. With the next thermal pulse, the temperature rises to $T_B=T_A+\Delta T$ and a new change in resistance $\Delta R_B$ is recorded, where $\Delta R_B$ arises from any desorption occurring during that pulse. As the temperature of the pulses ramps up further, i.e., to $T_C>T_B$ and beyond, analytes having a stronger sorption interaction with the sensor and less volatility will come off, causing a further change in the resistance, i.e., $\Delta R_C$, etc., until all of the sorbed analytes are gone from the sensor surface, at which point no further resistance changes will be observed. As shown in FIG. 11, different analytes will exhibit different desorption characteristics, and this will be reflected in the temperatures at which the changes in resistance are observed. Alternatively, one can sweep the pulse duration times with the temperature reached in each pulse held fixed in order to get directly at the kinetics, though because of thermal time constant limits the ability to study the kinetic behavior at very short times will be greatly limited.

When the full sweep is concluded, the resistance changes versus the pulse temperatures can be plotted as shown in FIG. 12B, with the plot representing a desorption spectrum for the sensor at the range of applied temperatures.

In the simplest cases, an isolated peak in the temperature spectrum like that illustrated in FIG. 12B would correspond to a single analyte as identified through control experiments with known vapors, and the size of the peak would be proportional to the concentration. If multiple peaks were present, then as in a TDS measurement, one at a higher temperature would correspond to a more volatile analyte. In distinguishing and identifying such peaks based on control experiments, a high temperature resolution may be needed and this would require a smaller ΔT. Finally, in the most complicated cases peaks would overlap and a numerical decomposition would be required based on fitting to a database, specific to the type of sensor used, that contained information regarding the resistance changes exhibited by various analytes versus temperature.

As further proof-of-principle of the concept depicted in FIGS. 12A and 12B, the inventors exposed to a vapor a chemielectric sensor/heater like that depicted in FIG. 5, where the sensor apparatus consisted of a sheet of graphene situated on an $SiO_2$ substrate, with two electrical contacts connecting the graphene sheet to a power source.

$SiO_2$ has extremely low thermal conductivity and so mimics a suspended structure, though the dissipated power will still be significantly higher than for a suspended structure. The graphene in the sensor system serves not only as the chemiresistive material but also, as described above, provides the thermal pulses via Joule heating when subjected to a bias voltage.

To test the device, the graphene was exposed to one of three analytes for a period of time so that significant absorption to the graphene surface occurred.

FIGS. 13A-13C illustrate an example wherein analytes on the graphene surface were detected and identified. As illustrated in FIG. 13A, immediately after exposing a graphene device configured as shown in FIG. 5 to a dilute vapor of nitromethane ($NO_2CH_3$), a thermal pulse train like the idealized depiction in FIG. 13A was applied while the resistance constantly monitored.

As can be seen from the plot in FIG. 13A, after 0.20 seconds, the full thermal pulse train successfully removed essentially all of the adsorbed nitromethane, as evidenced by the negligible changes in resistance exhibited for subsequent trains of thermal pulses. This means that at the end of the process the sensor was "cleared" and would be ready for a new sensing measurement. Observe also that the entire pulse train is executed in a mere 0.1 sec, which again is possible because of the high speed of this sensor/heater. This is of practical importance as a means of inducing rapid response and recovery in applications where the ambient is expected to change quickly, such as gradient-driven locating of a vapor-source, in mimicry of canine tracking, or high velocity transit through a vapor cloud, as on a mobile platform.

The inventors also analyzed how the resistance of the graphene sensor changed with the desorption of incident analytes as a function of the power applied to the sensor.

In this experiment, the graphene sensor configured as shown in FIG. 5 was exposed briefly to dilute nitrogen dioxide ($NO_2$) and dilute vapors of nitromethane ($NO_2CH_3$) and 2-nitrotoluene ($C_6H_4CH_3NO_2$), and the changes in the graphene sensor's resistance with the desorption of such analytes from voltage pulse sequences such as in FIG. 13A were determined as shown in FIG. 13B. The change in resistance between a point after exposure and before the voltage pulse started, and a short interval after concluding a particular voltage pulse, was recorded and plotted against the peak power dissipated in a particular pulse ($V^2/R$), and plotted in FIG. 13B.

As can be readily seen from inspection of the figure, the resistance change vs. power curves for the three analytes are quite different, with very different thresholds for the start of desorption, different signs for the change of resistance with power, and different ranges of power over which most of the recovery of device resistance to values prior to exposure occur. This clearly shows the technique capable of distinguishing analytes (selectivity), in a simplest way by comparing desorption thresholds as shown in FIG. 13C. A more sophisticated decomposition technique would use the entire temperature curves and consider variations of pulse length as well. This would be applied to mixtures of analytes and interferents, and would not only decide what is present but in what concentrations. Implementation would require computer algorithms likely using methods of machine learning in which the labeled data would be from experiments with single analytes in the laboratory.

The differences between analytes seen in FIGS. 13B and 13C provide the basis for the analyte selectivity of the present invention. For real mixtures containing multiple chemical species, the spectra could become quite complicated, and again machine learning methods would become necessary for analyzing the data.

The pulse sequence shown in FIG. 13A has several parameters which may be controlled at the discretion of the operator, whether human or computer. These parameters include thermal pulse width, first pulse amplitude, last pulse amplitude, and pulse-pulse temporal and power spacing. Additionally, the delay after the end of the pulse before resistance is sampled to generate curves such as shown in FIG. 13B may be varied. Control of these parameters might even be "on-the-fly" so that in response to initial observations the sensor/heater could be directed to examine critical regimes of time or temperature at higher resolution.

The approach just described has a base temperature of room temperature, and all operating temperatures are at that level or higher. Although one might conclude that the present invention would fail for analytes that are in the gas phase or are highly volatile vapors at room temperature, the inventors have observed that some chemielectric materials can respond well to such analytes. See J. T. Robinson, F. K. Perkins, E. S. Snow, Z. Q. Wei, and P. E. Sheehan, "Reduced Graphene Oxide Molecular Sensors," *Nano Letters* 8, 3137-3140 (2008), where a strong response to HCN was observed in graphene oxide chemiresistive sensors; see also the data shown in FIG. 13, where a response to $NO_2$ was observed and characterized with respect to sensor temperature. In addition, as discussed below, there are variations of the basic design to improve performance in the context of vapors with higher volatility.

Advantages and New Features

The invention described herein provides a new approach to chemielectric point sensing that enhances their sensitivity and selectivity by enabling them to function at higher frequencies than the quasi-dc conditions of all previous approaches. The advantages and new features of the method and device over existing approaches may be summarized as follows:

The present invention provides a chemielectric sensor system with an apparatus design and a measurement methodology that is not specific to a single type of point-sensor but can be applied to many different types so long as the sensor is effective over a moderate temperature range. Applicable transducers in a sensor system in accordance with the present invention can include MIME sensors based on organic functionalized gold nanoclusters, organic molecular and polymer semiconductor chemiresistors, carbon nanotube chemiresistors and chemicapacitors, graphene oxide platelet chemiresistors, graphene chemiresistors, TMD chemiresistors, all proven and developed chemical vapor sensing technologies.

This general technique is also not specific to a particular analyte or even class of analyte, but rather is effective in identifying multiple targets, and discriminating them against a complex multiple component background. It may even be used to heuristically identify-to-warn against unknown analytes on the basis of interaction energies that are similar to known dangerous compounds.

A sensor system in accordance with the present invention lowers the noise floor of chemielectric point-sensors by taking the measurements of the electrical property of the sensor element at a frequency $f_m$ greater than the corner frequency $f_c$ known in the art below which the 1/f noise of the sensor becomes dominant. By so operating outside the low-frequency 1/f-dominated regime, the signal-to-noise ratio of the sensor is increased, which allows measurement of smaller signals and hence results in higher sensitivity.

A sensor system in accordance with the present invention also greatly enhances the selectivity of chemielectric point-sensors by exploiting differences in the desorption thermokinetics of various analytes and interferents for a given sensor. Use of multiple, differently functionalized sensors in this mode would broaden the space even further.

A sensor system in accordance with the present invention also provides advantages from a detection system perspective in that it eliminates the need for a scrubbed air supply, a preconcentrator, and a micro-gas-chromatograph. All of these simplifications serve to reduce the system size, weight, power, and cost. Also, this simplification reduces possible sources of error while increasing reliability.

A sensor system in accordance with the present invention requires only a small form factor with simple implementation size adaptable for garment, badge, and small vehicle attachments for unobtrusive but effective monitoring, and for handheld or autonomous applications.

A sensor system in accordance with the present invention can also serve as its own preconcentrator and micro-gas-chromatograph. For the former, one simply uses the sensor itself as the concentrator, leaving it exposed for as long a collection time as desired. And for the latter, the thermal desorption process replaces the differentiation of analytes that would occur in micro-gas-chromatograph. Clearly, the high-speed thermally pulsed sensor permits much simplification of a chemical vapor detection system.

A sensor system in accordance with the present invention has a low unit cost combined with relatively high speed and autonomous operation can allow networked system of dense sensors for mapping urban or crowded environments.

In addition, the sensor technique in accordance with the present invention is versatile. For example, if operated in a manner illustrated in FIG. 10, the sensitivity of the sensor can be increased by decreasing the frequency of the thermal pulses so as to increase the low-temperature accumulation time, while, in contrast, the speed of the sensor can be optimized at the expense of sensitivity by increasing the thermal pulse cycle rate.

The versatility of the sensor design and approach in accordance with the present invention also allows adjustment in real time by an operator or a smart controller to implement a form of "attention" in the event of an anomaly, or to switch instantly between a sensitive, slow, and low power "observer" mode and a fast, high power mode as needed by the detection situation.

Parametric analysis is an established technique for resolving sensor data. Published descriptions rely on equilibrium data from sensor responses. In the invention disclosed here, the addition of dynamic parameters such as rate of response and recovery, static parameters such as the initiation, termination, and magnitude of the response change with temperature, as well as ultimately the multiple equilibrium values of response at multiple temperatures adds greatly to the dimensions of space for parametric analysis.

Alternatives

The invention as stated is best for differentiating between analytes that show significant absorption on the sensor at room temperature. This allows it to be sensitive to a wide range of analytes as noted earlier. In addition, there are alternatives that could allow the range to be expanded even further. One would involve cooling the sensor so that its base temperature was lower than room temperature. Small Peltier coolers are available that could be used for this purpose and the power expenditure might not be so great in a suspended design. A second alternative would be to functionalize the sensor surface in order to make it a stronger (and potentially more selective) adsorber of the analyte(s) of interest, e.g., nitrogen dioxide as shown in FIG. 13. This is especially easy to do in the class of MIME sensors based on easily functionalized gold nanoclusters.

In addition, as noted above, although in many embodiments, e.g., where the sensor is fabricated on top of a multilayer composed structure, the sensor element can be disposed on a heater element that is isolated within and supported by an insulating air bridge, in other embodiments, it is not. For example, a sensor system in accordance with one or more aspects of the present disclosure can include a sensor fabricated from a reduced graphene oxide platelet assemblage, where the oxide is etched out from under it, leaving a bridge comprising the sensor spanning the gap between two electrodes.

In other embodiments, the sensor can be in the form of an Au cluster, where the bridge is fabricated from a uniform metal ribbon with $S_3N_4$ deposited on top, mostly in the middle, with two electrodes and the Au cluster deposited on top of the $S_3N_4$. In such a case, the bridge is electrically insulated from the sensor but is not thermally isolated, and will heat and cool rapidly.

Obtaining selectivity in a chemical vapor sensor is a challenge under any circumstance and it is not expected that this invention will be a cure-all. As a result, it is likely to be a useful alternative to implement the high bandwidth sensing approach of this invention in an array format that would include multiple sensors with varying functionalities and selectivities.

Although particular embodiments, aspects, and features have been described and illustrated, one skilled in the art would readily appreciate that the invention described herein is not limited to only those embodiments, aspects, and features but also contemplates any and all modifications and alternative embodiments that are within the spirit and scope of the underlying invention described and claimed herein. The present application contemplates any and all modifications within the spirit and scope of the underlying invention described and claimed herein, and all such modifications and alternative embodiments are deemed to be within the scope and spirit of the present disclosure.

What is claimed is:

1. A chemielectric sensor apparatus, comprising:
   a substrate; and
   a sensor/heater assembly disposed on the substrate, the sensor/heater assembly comprising:
      a chemielectric sensor element configured to sorb an analyte from a vapor incident on a surface of the sensor element; and
      a heater element configured to apply a predetermined plurality of thermal pulses having a duration of 0.1 sec or less to the sensor element, each of the thermal pulses being configured to heat the sensor element to a corresponding predetermined temperature $T_t$, wherein the thermal pulses are applied to the sensor element at a predetermined frequency $f_p$ 10-1000 Hz or higher as allowed by the thermal time constant of the sensor element, a time between each of the thermal pulses being greater than the sum of (a) a time needed for the sensor element to reach a predetermined temperature, (b) a time at which the sensor element remains at the predetermined temperature after the application of each pulse, and (c) a time needed for the sensor element to return to a predetermined baseline temperature, the thermal pulses causing at least some of the sorbed analyte to desorb from the surface of the sensor element; and
      a means for measuring a first value of an electrical property of the sensor element before application of each thermal pulse and for measuring a second value of the electrical property of the sensor element after application of each thermal pulse, the measurements of the electrical property being taken at a predetermined frequency $f_m$ that is greater than a corner frequency $f_c$ of an 1/f noise floor of the sensor apparatus,
   differences between the first and second values over the entire plurality of thermal pulses forming a spectrum of values;
   wherein a predetermined range of differences between the first and second values of the electrical property within the spectrum is indicative of a presence of a specified analyte in the vapor; and
   wherein the frequency of the pulses $f_p$ and the frequency of the measurements $f_m$ are configured to provide a predetermined sensitivity of the sensor to the presence of the specified analyte.

2. The chemielectric sensor apparatus according to claim 1, further comprising an intake mechanism configured to receive vapor from an ambient atmosphere and pass the vapor over the sensor/heater assembly.

3. The chemielectric sensor apparatus according to claim 2, further comprising a pump configured to pull an ambient atmosphere through the intake and pass it across the sensor/heater assembly.

4. The chemielectric sensor apparatus according to claim 1, wherein the sensor element is situated on a surface of an air bridge material that is thermally isolated from the substrate by means of an air gap between the substrate and the air bridge material; and
   wherein the heater element comprises a resistive wire situated within the air bridge material, the heater element being electrically isolated from the sensor, the resistive wire being coupled to a power source configured to provide Joule heating to the sensor element.

5. The chemielectric sensor apparatus according to claim 4, wherein the sensor element comprises a transductive material deposited on the air bridge material.

6. The chemielectric sensor apparatus according to claim 1, wherein the sensor/heater assembly is situated on an electrically insulating and thermally conducting material layer; and
   wherein the heating element comprises a resistive wire situated between the electrically insulating material layer and the substrate, the resistive wire being coupled to a power source configured to provide Joule heating to the sensor element.

7. The chemielectric sensor apparatus according to claim 6, wherein the sensor element comprises functionalized gold nanoparticles, carbon nanotube random networks deposited on an insulating substrate, reduced graphene oxide platelets, graphene films, transition metal dichalcogenide mono- or few-layer films, or a metal oxide nanostructured material.

8. The chemielectric sensor apparatus according to claim 6, wherein the electrically insulating and thermally conducting material layer comprises $Si_3N_4$, $SiO_2$, or $Al_2O_3$.

9. The chemielectric sensor apparatus according to claim 6, wherein the substrate comprises a $SiO_2$ layer on a silicon wafer.

10. The chemielectric sensor apparatus according to claim 1, wherein the sensor/heater assembly is situated directly on an electrically insulating surface of a thermally conducting substrate;
   the sensor element being coupled to a controllable power source and being configured to self-heat upon an application of voltage from the power source.

11. The chemielectric sensor apparatus according to claim 10, wherein the sensor element comprises a graphene sheet, the graphene sheet being contacted to the power source by electrical contacts to the graphene sheet.

12. The chemielectric sensor apparatus according to claim 10, wherein the substrate comprises $SiO_2$, glass, or plastic.

13. The chemielectric sensor apparatus according to claim 1, comprising a plurality of sensor/heater assemblies situated on a single substrate.

14. A method for detecting a presence of an analyte in an ambient atmosphere, comprising:
- exposing a chemielectric sensor element to an ambient atmosphere, the sensor element being configured to sorb an analyte from the atmosphere onto a surface of the sensor element and to exhibit a change in an electrical property of the sensor upon a desorption of the analyte from its surface;
- applying a controlled plurality of thermal pulses having a duration of 0.1 sec or less to the sensor element, each of the thermal pulses being configured to raise a temperature of the sensor element to a corresponding predetermined $T_i$, wherein the thermal pulses are applied to the sensor element at a predetermined frequency $f_p$ of 10-1000 Hz or higher as allowed by the thermal time constant, a time between each of the thermal pulses being greater than the sum of (a) a time needed for the sensor element to reach a predetermined temperature, (b) a time at which the sensor element remains at the predetermined temperature after the application of each pulse, and (c) a time needed for the sensor element to return to a predetermined baseline temperature, the thermal pulses causing at least some of the sorbed analyte to desorb from the surface of the sensor element; and
- measuring a first value of an electrical property of the sensor element before application of each thermal pulse and for measuring a second value of the electrical property of the sensor element after application of each thermal pulse, the measurements of the electrical property being taken at a predetermined frequency $f_m$ that is greater than a corner frequency $f_c$ of an 1/f noise floor of the sensor apparatus,
- differences between the first and second values over the entire plurality of thermal pulses forming a spectrum of values; and
- wherein a predetermined range of differences between the first and second values of the electrical property within the spectrum is indicative of a presence of a specified analyte in the vapor; and
- wherein the frequency of the pulses $f_p$ and the frequency of the measurements $f_m$ are configured to provide a predetermined sensitivity of the sensor to the presence of the specified analyte.

15. The method according to claim 14, wherein each successive thermal pulse in the plurality of thermal pulses is configured to successively raise the temperature of the sensor element, the value of the electrical property having a corresponding change with each change in temperature of the sensor element, the method further including the steps of measuring the change in the value of the electrical property until the value no longer changes.

16. The method according to claim 14, wherein a specified pattern of values in the spectrum is indicative of a specified analyte in the atmosphere, and further wherein a magnitude of values in the spectrum is indicative of a concentration of the specified analyte in the atmosphere.

17. The method according to claim 14, further comprising mapping the changes between the first and second measurements of the resistance of the sensor element to the temperature, duration, and/or frequency of the thermal pulses to determine a concentration of the analyte that is indicated by a given combination of temperature, duration, and/or frequency of the thermal pulses.

* * * * *